United States Patent [19]
Suzuki et al.

[11] 4,331,699
[45] May 25, 1982

[54] METHOD FOR EVALUATING ELECTROLESS PLATING

[75] Inventors: Masayuki Suzuki, Yokohama; Yuichi Sato, Atsugi; Ken-ichi Kanno, Tokyo, all of Japan

[73] Assignee: Tokyo Shibaura Denki Kabushiki Kaisha, Japan

[21] Appl. No.: 125,567

[22] Filed: Feb. 28, 1980

[30] Foreign Application Priority Data

Mar. 7, 1979 [JP] Japan ................................. 54-25670

[51] Int. Cl.³ ............................................. C23C 3/02
[52] U.S. Cl. .................................... 427/8; 324/71 R; 427/9; 427/10; 427/443.1
[58] Field of Search .................................... 427/8–10, 427/443.1; 324/71 R

[56] References Cited

U.S. PATENT DOCUMENTS

4,125,642  11/1978  Petit et al. ............................... 427/8

OTHER PUBLICATIONS

Paunovic, "An Electrochemical Control System for Electroless Copper Bath", 127 J. Electrochem. Soc. 365, Feb. 1980.
Paunovic, "Electrochemical Aspects of Electroless Deposition of Metals", Plating, Nov. 1978.
Delahay, "Coulostatic Method for the Kinetic Study of Fast Electrode Processes . . . ", J. Phys. Chem., 66, 2204 (1962).
Ohno, "An Application of the Polarization Resistance Method to the Determination of the Rate of Copper Deposition in an Electroless Plating Bath", Kinzoku Hyomen Gijutsu, 29, 600, (1978).

*Primary Examiner*—John D. Smith
*Attorney, Agent, or Firm*—Finnegan, Henderson, Farabow, Garrett & Dunner

[57] ABSTRACT

A test piece is immersed in an electroless plating bath. It is then electrically charged instantaneously via a counter electrode to have a polarization potential $\eta(t)$ of a few millivolts. The charge consumed by the electroless plating reaction of the test piece is measured by a potential recorder in the form of a variation of the polarization potential $\eta(t)$ with respect to time t. The $\eta(t)-t$ relation is analyzed to obtain a resistance R of the test piece. After the potential of the test piece has returns to electroless deposition potential $E_{ELP}$, the test piece is charged again until its polarization potential $\eta(t)$ rises to 50 millivolts or more. A $\eta(t)-t$ relation is obtained. Based on the $\eta(t)-t$ relation, a Tafel slope $\beta_a$ of anodic reaction is obtained. After the potential of the test piece has returned to electroless deposition potential $E_{ELP}$, the test piece is so charged for the third time as to have its polarization potential $\eta(t)$ lowered to $-50$ millivolts or less, and a $\eta(t)-t$ relation is obtained. This relation is analyzed to obtain a Tafel slope $\beta_c$ of anodic reaction of the test piece. Based on the reaction resistance R, Tafel slopes $\beta_a$ and $\beta_c$, an electroless plating current density $I_{ELP}$ is obtained. Based on the electroless plating current density $I_{ELP}$, a rate of electroless plating $V_{ELP}$ is calculated.

22 Claims, 19 Drawing Figures

$\eta_R(t)$-t CURVE $\log \eta_R(t)$-t CURVE

F I G. 13
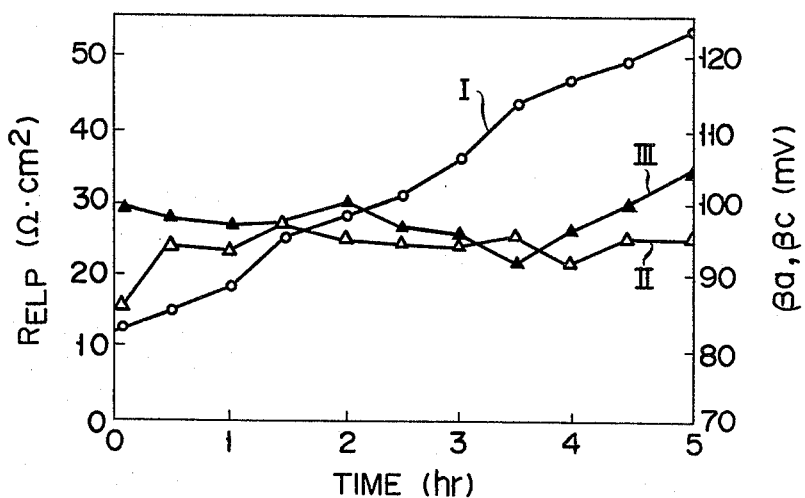
F I G. 14
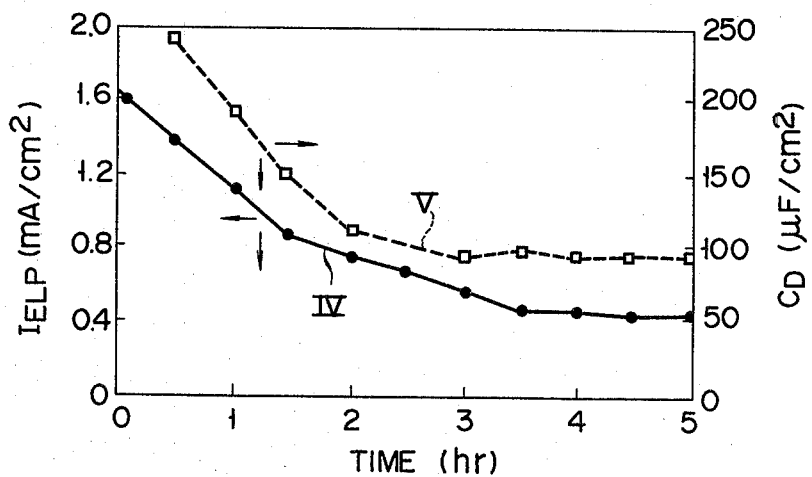

METHOD FOR EVALUATING ELECTROLESS PLATING

This invention relates to a method and apparatus for evaluating electroless plating, more specifically the rate of electroless plating, the weight of a metal layer formed by the plating (or thickness thereof), the surface condition of the metal layer, the chemical composition of a plating bath used, the adhesion of the metal film, and so forth. In particular the invention relates to a method and apparatus for detecting the speed of electroless plating, using coulostatic method.

The inventors of this invention have obtained U.S. Pat. No. 4,130,464 and have filed U.S. patent application Ser. No. 950,051. In these U.S. patent and U.S. patent application they proposed methods of evaluating the corrosion rate of metal, which utilize coulostatic method. According to this invention, coulostatic method is applied to electroless plating.

Methods are known which detect the rate of electroless plating or chemical plating. Methods for measuring the thickness of a metal film formed by such plating are also known. Further, various methods for detecting the chemical property of a plating bath are known.

In a known method a micrometer is used to measure the thickness of a metal layer formed by electroless plating or chemical plating. In another known weight gain method a metal layer weight formed by electroless plating is obtained based on the difference between the weight of a substrate before the plating and the weight of the substrate after the plating. With both methods it takes a long time to detect the thickness of a metal layer. Further, with these methods it is difficult to measure other factor of electroless plating, such as the change of rate of plating.

A method is known which detects pH, temperature and metal ion concentration of a plating bath. However, it is difficult with this method to detect an accurate rate of plating. The method is therefore not effective in controlling the chemical property of a plating bath.

Also known is a method which estimates the plating rate on the basis of the electroless deposition potential $E_{ELP}$ of a substrate immersed in a plating bath, since electroless plating is a kind of electrochemical reaction, a combination of the anodic oxidation of a reducing agent and the cathodic reduction of metal ion. This method, however, does not directly measure the plating rate, and the measured potential is affected by other factors. In some cases it is difficult with the method to estimate the plating rate accurately.

Further, Izumi Ohno "kinzoku Hyomen Gijutsu", 29, 600, 1978 discloses a method for estimating a plating rate. In this method a slight polarization is caused on a metal test piece immersed in a plating bath, and a deposition resistance $R_{ELP}$ of the test piece is obtained based on the relationship between the polarization potential of the test piece and the current. With this method, however, current must flow through the test piece for a relatively long time. This would destroy the natural plating condition. Further, in the case of electroless plating, the reaction resistance is not sufficiently large to neglect the solution resistance of the plating bath. The solution resistance of the plating bath cannot therefore be negligible in comparison with the reaction resistance and will probably lead to an incorrect plating rate estimate. Moreover, since the measurement is restricted to the reaction resistance $R_{ELP}$, it is impossible with this method to detect the surface condition of the metal film, the condition of the plating bath or the adhesion of the metal film to the test piece. To make the matter worse, the plating rate estimated by this method turns out to be incorrect in most cases.

As mentioned above, various methods are known, each for detecting or estimating one of the conditions of electroless platings. Each of the methods is practically disadvantageous. No method that can evaluate various electroless plating conditions has ever been proposed.

An object of this invention is to provide a method and apparatus for evaluating electroless plating, both accurately and quickly.

This invention provides a method of evaluating electroless plating comprising a step of determining the reaction resistance $R_{ELP}$ of a test piece having a surface area S and disposed in a electroless plating bath, said step comprising:

(i) instantaneously feeding a given charge $q_R$ to the electrical double layer of the test piece, thereby changing the potential of the test piece to have a predetermind polarization potential $\eta_R$;

(ii) detecting, as a function of time, the variation of the polarization potential $\eta_R(t)$ of the test piece due to an electroless plating reaction, using a reference electrode disposed in the plating bath;

(iii) determining an initial polarization potential $\eta_R(0)$ of the test piece upon completion of the charge supply $\eta(t=0)$, based on the polarization potential $\eta_R(0)$ detected as a function of time; and (iv) calculating the reaction resistance $R_{ELP}$ based on the given charge $q_R$, initial polarization potential $\eta_R(0)$, surface area S, and the slope of log $\eta_R(t) - t$ relation, the reaction resistance being inversely proportional to the rate of electroless plating $V_{ELP}$;

whereby the electroless plating is evaluated by the value of reaction resistance.

This invention can be more fully understood from following detailed description when taken in conjunction with the accompanying drawings, in which:

FIGS. 13 to 17 are graphs showing values actually detected by a method of evaluating electroless plating according to this invention;

Figure 1:
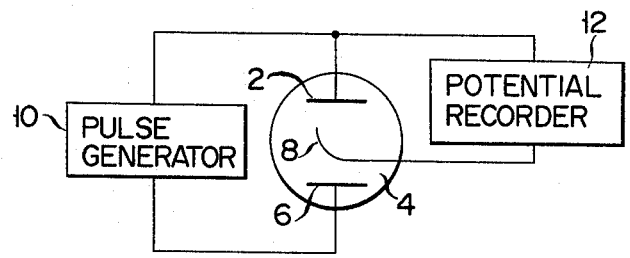
FIG. 1 is a block diagram of an apparatus for carrying out a method of evaluating the electroless plating according to this invention.

A method of measuring the rate of electroless plating according to this invention is an application of coulostatic method, wherein the rate of electroless plating is analyzed based on the measurements obtained by such a measuring apparatus as illustrated in FIG. 1. In the coulostatic method, the interface between an electrode and a solution acts as a leaky capacitor. An electrical double layer at the interface is instantaneously charged with a given amount of charge. The process of consuming the given charge by the electrode reaction is recorded as a variation of electrode potential with respect to time. The rate of the electrode reaction is calculated based on the recorded data.

The measuring apparatus shown in FIG. 1 is designed to detect how the polarization potential $\eta_R(t)$ and time $t$ is recorded by a potential recorder 12 three times under different conditions, thereby obtaining the three $\eta_R(t)-t$ curves. The $\eta_R(t)-t$ curves are analyzed to obtain the reaction resistance $R_{ELP}$ of the test piece 2, a Tafel slope $\beta_a$ of anodic reaction and a Tafel slope $\beta_c$ of cathodic reaction, respectively. Based on the reaction resistance $R_{ELP}$, Tafel slope $\beta_a$ and Tafel slope $\beta_c$, an electroless plating current density $I_{ELP}$ is calculated by the following formula:

$$I_{ELP}=(K/2.3)/R_{ELP},$$

$$\text{where } K=\beta_a\beta_c/(\beta_a+\beta_c) \tag{1}$$

Based on $I_{ELP}$, the rate of electroless plating $V_{ELP}$ is obtained by the following formula:

$$V_{ELP}=(M/n\cdot F)\,I_{ELP} \tag{2}$$

In equation (2), M denotes the atomic weight of metal deposited on the test piece 2, n the valence of the deposited metal ion, and F the Faraday constant.

If it takes time $\tau$ to carry out the electroless plating, the quantity of charges $Q_{ELP}$ consumed by the plating is expressed by the following formula:

$$Q_{ELP} = \int_0^\tau I_{ELP}\,dt \tag{3}$$

Further, the weight $W_{ELP}$ of metal deposited is expressed by the following formula:

$$W_{ELP}=(M/n\cdot F)Q_{ELP} \tag{4}$$

Where $W_{ELP}$ is of course weight of metal per unit surface area of the test piece 2, whose surface area is S. The thickness $d_{ELP}$ of the metal film deposited on the test piece 2 can therefore be obtained by the following formula:

$$d_{ELP}=W_{ELP}/\rho \tag{5}$$

In equation (5) $\rho$ denotes the specific gravity of the metal deposited on the test piece 2.

As will later be described, it is possible to detect how strongly the deposited metal adheres to the test piece 2, based on the variation of the reaction resistance $R_{ELP}$ during the electroless plating reaction. Also as will later be described, it is possible to evaluate the surface condition of the deposited metal film and the plating bath, based on differential capacitance $C_D$ which is obtained when the reaction resistance $R_{ELP}$ is analyzed.

In practice, the rate of electroless plating and other factors of electroless plating are detected in the following manner.

The surface area S of the test piece 2 is measured, and the test piece 2 is put into a cell 4 filled with a plating bath. The test piece 2 functions as a working electrode. Preferably, it is a piece of metal to be plated. It may be a piece of nonmetallic material, e.g. plastics. If the test piece 2 is nonmetallic, an electrode terminal (not shown) is attached to the test piece 2 so that is may be electrically connected to a metal layer to be deposited on the test piece 2. In this case, the metal layer deposited on the test piece 2 functions as a working electrode.

A counter electrode 6 is disposed in the cell 4. Between the test piece 2 and the counter electrode 6 a reference electrode 8 is arranged. The reference electrode 8 is made of copper (Cu), nickel (Ni), platinum (Pt), palladium (Pd), chromium (Cr), rhodium (Rh), iridium (Ir) or the like. Preferably, it is made of the same material as the test piece 2. If the electrodes 8 and the test piece 2 are made of the same material, their natural potentials, i.e. electroless deposition potentials $E_{ELP}$ are substantially equal, thus rendering it unnecessary to apply a bias voltage to cancel their natural potentials. The counter electrode 6 is made of copper (Cu), nickel (Ni), platinum (Pt), palladium (Pd) or the like. These electrodes 2, 6 and 8 may be shaped in various ways. For example, they are shaped like rods or plates.

Between the test piece 2 and the counter electrode 6 there is connected a pulse generator 10 to apply a predetermined charge. Between the test piece 2 and the reference electrode 8 there is connected a potential recorder 12 to detect the polarization potential $\eta_R(t)$ of the test piece 2. The recorder 12 has a high input impedance. The potential recorder 12 records three $\eta_R(t)-t$ curves under different conditions, so that the reaction resistance $R_{ELP}$, anodic Tafel slope $\beta_a$ and cathodic Tafel slope $\beta_c$ may be obtained. A first $\eta_R(t)-t$ curve is analyzed to obtain the reaction resistance $R_{ELP}$, a second $\eta_R(t)-t$ curve to obtain anodic Tafel slope $\beta_a$, and the third $\eta_R(t)-t$ curve to obtain cathodic Tafel slope $\beta_c$.

First, it will be described how to obtain the reaction resistance $R_{ELP}$. Via the counter electrode 6 a predetermined charge $q_R$ is applied to the test piece 2 for a short time, such as several microseconds, to a few milliseconds, thus charging instantaneously the electrical double layer of the test piece 2. The charge $q_R$ is of such a positive value or negative value as to raise the polarization potential $\eta_R(t)$ of the test piece 2 by not more than 30 millivolts, preferably by 10 millivolts or less. The charge $q_R$ on the electrical double layer is consumed by an electroless plating reaction of the test piece 2. As a result, the potential $\eta_R(t)$ of the test piece 2 varies with time to the natural potential, electroless deposition potential $E_{ELP}$. This potential variation is detected by using the reference electrode 8 and recorded by the potential recorder 12, thereby obtaining such $\eta_R(t)-t$ curve as shown in FIG. 2 and also such log $\eta_R(t)-t$ curve as shown in FIG. 3.

Since the potential recorder 12 has a high input impedance, the current flowing from the test piece 2 to the recorder 12 via the reference electrode 8 can be neglected. The polarization potential $\eta_R(t)$ of the test piece 2 can therefore be considered to be measured by an open circuit, and the decay of the polarization potential $\eta_R(t)$ can be regarded as having been caused by the electroless plating reaction of the test piece 2 alone.

Figure 2:
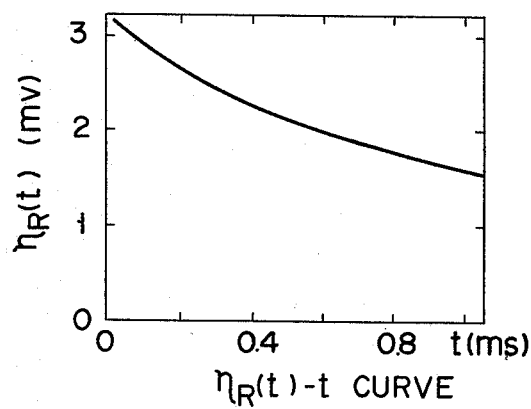
FIGS. 2 and 3 are graphs showing the relationship between a lapse of time t and a polarization potential $\eta_R(t)$ measured by the method according to this invention.
Figure 3:
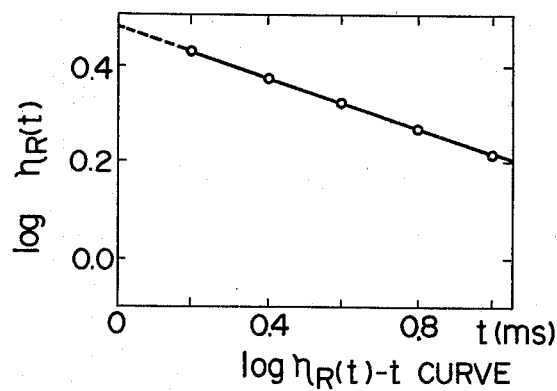

The $\eta_R(t)-t$ curve illustrated in FIG. 2 is analyzed to obtain the reaction resistance $R_{ELP}$ of the test piece 2 in the following manner. The potential of the test piece 2 in the plating bath is first at the electroless deposition potential $E_{ELP}$. When its electrical double layer is instantaneously charged with charge $q_R$, the potential rises until it reaches a maximum potential $E_{mes}$. The initial polarization potential $\eta_R(0)$ of the test piece 2 is then expressed as follows:

$$\eta_R(0) = E_{mes} - E_{ELP} \quad (6)$$

The initial polarization potential $\eta_R(0)$ cannot be measured directly by the potential recorder 12 because the ohmic drop of the resistance $R_s$ of the test plating bath gives incorrect measurement. The variation of the polarization potential $\eta_R(t)$ with respect to time recorded by the recorder 12 is theoretically given by the following formula:

$$\eta_R(t) = \eta_R(0) \exp(-t/C_D \cdot R_{ELP}) \quad (7)$$

A derivation of the equation (7) will be referred to hereinafter.

Equation (7) may be transformed into the following logarithmic equation:

$$\log \eta_R(t) - \log \eta_R(0) = -t/2.3\, C_D \cdot R_{ELP} \quad (8)$$

In equation (8), $C_D$ is the differential capacitance of the test piece 2. The values of both $C_D$ and $R_{ELP}$ are given per unit surface area of the test piece 2. The differential capacitance $C_D$ may be expressed as follows:

$$C_D = \Delta q_R / \eta_R(0) \quad (9)$$

In equation (9), $\Delta q_R = q_R/S$. Where $q_R$ denotes a charge and S denotes the surface area of the test piece 2. The differential capacitance $C_D$ varies depending on the potential of the test piece 2. But it is considered substantially constant within a small potential domain.

The reaction resistance $R_{ELP}$ is calculated from the data recorded by the recorder 12 and by equations (8) and (9). Equation (8) represents a rectilinear line and the log $\eta_R(t)-t$ curve is linearly plotted on a semilogarithmic graph shown in FIG. 3. Thus, the initial potential $\eta_R(0)$ of the test piece 2 is obtained by extrapolating the rectilinear line to the time $t=0$. The differential capacitance $C_D$ is obtained by substituting the initial polarization potential $\eta_R(0)$ into equation (9). Based on the slope of the rectilinear line in FIG. 3 and the differential capacitance $C_D$, the reaction resistance $R_{ELP}$ can be therefore obtained.

Figure 4:
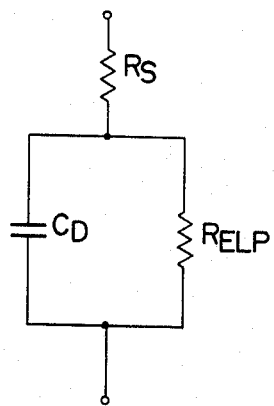
FIG. 4 shows an equivalent circuit of the electroless plating reaction in the cell shown in FIG. 1.

The electroless plating reaction of the test piece 2 in the plating bath may be electrically represented in the form of such an equivalent circuit shown in FIG. 4. The resistance $R_s$ of the plating bath serves as a resistor to the electric current which flows when the differential capacitance $C_D$ is charged up. To measure the reaction resistance $R_{ELP}$, the polarization potential $\eta_R(t)$ is detected by substantially an open circuit. The measured value of the reaction resistance $R_{ELP}$ is therefore never affected by the bath resistance $R_s$. If the measured value of the resistance $R_{ELP}$ is affected slightly by the bath resistance $R_s$, the initial polarization potential $\eta_R(0)$ can be obtained correctly by extrapolation. If the equivalent circuit of FIG. 4 and equation (7) are compared, it will be understood that the electroless plating reaction can be electrically detected in the form of a transient phenomenon in a closed circuit consisting of the capacitor $C_D$ and the resistor $R_{ELP}$. That is, the electroless plating reaction can be said to be a phenomenon in which the charge density $\Delta q_R$ of the charged capacitor $C_D$ is consumed in the resistor $R_{ELP}$.

The theoretical derivation of equations (1) and (7) will be given to facilitate a better understanding of these equations.

Generally, electroless plating is known as a kind of electrochemical reaction, a combination of the anodic oxidation of a reducing agent and the cathodic reduction of metal ion. That is, the electroless plating is believed to take place when the anodic oxidation (Red$\rightarrow$OX+ne) of a reducing agent and the cathodic reduction ($M^{n+}$+ne$\rightarrow$M) of metal ion proceed at the same time, with the same current and thus developing at the same speed. The current during the electroless plating is called "electroless deposition current density $I_{ELP}$", and the potential built up during the plating is called "electroless deposition potential $E_{ELP}$". As the potential is elevated from the electroless deposition potential $E_{ELP}$, such relationship as expressed by the following equation (10) will be established between the polarization potential $\eta(t)$ and the external current I(t), i.e. Faradaic current density:

$$I(t) = I_{ELP}\left[\exp\left(\frac{\alpha_a nF}{RT}\eta(t)\right) - \exp\left(-\frac{\alpha_c nF}{RT}\eta(t)\right)\right] \quad (10)$$

$$= I_{ELP}\left[\exp\left(\frac{2.3}{\beta_a}\eta(t)\right) - \exp\left(-\frac{2.3}{\beta_c}\eta(t)\right)\right]$$

That is, equation (10) represents electroless plating reaction. In equation (10), R denotes gas constant, T the absolute temperature, $\beta_a = 2.3 \cdot RT/\alpha_a nF$ and $\beta_c = 2.3 \cdot RT/\alpha_c nF$. If $\eta \ll \alpha_a nF/RT$ and $\eta \ll \alpha_c nF/RT$, equation (10) will be transformed into equation (11). In other words, if the polarization potential $\eta_R(t)$ is assumed to be within less than 30 millivolts and more than $-30$ millivolts, the following Stern-Geary equation (11) is established. The variation of the polarization potential $\eta_R(t)$ within this degree is a necessary condition for obtaining the reaction resistance $R_{ELP}$.

$$I(t) = 2.3 I_{ELP}(\beta_a + \beta_c)/\beta_a \beta_c \eta_R(t) \quad (11)$$

In view of equation (11), equation (1) can be transformed into the following equation:

$$\eta_R(t) = I(t) \cdot R_{ELP} \quad (12)$$

Thus, if equations (11) and (12) are combined, the following equation will be established:

$$I_{ELP} = \frac{\beta_a \beta_c}{2.3(\beta_a + \beta_c)} \cdot \frac{1}{R_{ELP}} = \frac{K}{2.3} \cdot \frac{1}{R_{ELP}} \quad (1)$$

Equation (7) is derived from equation (11) in the following manner.

The charge density $\Delta q_R$ consumed by the electroless plating reaction from time 0 to time t can be expressed as follows:

$$\Delta q_R = C_D(\eta(0) - \eta(t)) \quad (13)$$

The charge density $\Delta q_R$ can also be expressed from the equation (11) by the following equation:

$$\Delta q_R = \int_0^t I(t)dt = \int_0^t 2.3\{(\beta_a + \beta_c)/\beta_a\beta_c\}\eta(t) \cdot I_{ELP} dt \quad (14)$$

From equations (13) and (14) the following differential equation is derived.

$$-C_D \cdot (d\eta_R(t)/dt) = 2.3\{(\beta_a+\beta_c)/\beta_a\beta_c\}\eta(t)\cdot I_{ELP} \quad (15)$$

Solving the equation (15) under the initial condition that $\eta(t)=\eta(0)$ at $t=0$, we can derive the following equation:

$$\eta(t)=\eta(0)\exp[-2.3 I_{ELP} t/(C_D K)] \quad (16)$$

where $K=\beta_a\beta_c/(\beta_a+\beta_c)$ and $\beta_a$ and $\beta_c$ are Tafel slopes of anodic and cathodic reaction respectively. As seen from the equation (1), $K/2.3 \cdot I_{ELP}$ may be replaced by $R_{ELP}$. Using the resistance $R_{ELP}$ in place of $K/2.3 \cdot I_{ELP}$ leads to the equation (7) mentioned above.

$$\eta_R(t)=\eta_R(0)\exp[-t/(C_D \cdot R_{ELP})] \quad (7)$$

Accordingly, the polarization resistance $R_{ELP}$ can be calculated based on the slope of the rectilinear line in FIG. 3 and the differential capacitance $C_D$, which has been calculated based on the charge density $\Delta q_R$ and the initial polarization potential $\eta_R(0)$.

Now it will be described how to record the second $\eta_{\beta a}(t)-t$ curve from which to obtain anodic Tafel slope $\beta_a$. Via the counter electrode 6, a predetermined charge $q_{\beta a}$ is applied to the test piece 2 for a short time for example, several microseconds to a few milliseconds, thus charging instantaneously the electrical double layer of the test piece 2. The charge $q_{\beta a}$ is larger than the charge $q_R$ applied to the test piece in order to obtain the reaction resistance $R_{ELP}$. More specifically, the charge $q_{\beta a}$ is of such a value as to elevate the polarization potential $\eta_{\beta a}(t)$ of the test piece 2 to 30 millivolts or more, preferably to 50 millivolts or more. The charge $q_{\beta a}$ is used up by the electroless reaction of the test piece 2, and the potential of the test piece 2 gradually varies with time. This potential variation is detected by using the reference electrode 8 and recorded by the potential recorder 12, thereby obtaining such a $\eta_{\beta a}(t)-t$ curve shown in FIG. 5.

In a similar way, the third $\eta_{\beta c}(t)-t$ curve from which to obtain cathodic Tafel slope $\beta_c$ is recorded. Namely, a predetermined charge $q_{\beta c}$ of the opposite polarity to the charge $q_{\beta c}$ is applied through the counter electrode 6 to the test metal piece for such a short time as several microseconds to a few milliseconds. The charge $q_{\beta c}$ is of such a value as to lower the polarization potential $\eta_{\beta c}(t)$ of the test piece 2 to tens of minus millivolts, preferably to $-50$ millivolts or less.

The three $\eta_{\beta a}(t)-t$ curves need not be obtained in the above-mentioned order. But it is desired that a charge should not be applied to the test piece 2 until the potential of the test metal 2 returns to the natural potential, i.e. electroless deposition potential $E_{ELP}$. To bring the potential of the test piece 2 quickly back to the electroless deposition potential $E_{ELP}$, a backward bias may be applied to the test piece 2.

It will now be explained how to obtain the Tafel slope $\beta_a$ of anodic reaction and the Tafel slope $\beta_c$ of cathodic reaction from the second $\eta_{\beta a}(t)-t$ curve and third $\eta_{\beta a}(t)-t$ curves.

If the polarization potential $\eta_{\beta a}(t)$ of the test piece 2 rises to not less than 30 milliseconds, preferably 50 millivolts or more, in order to obtain the anodic Tafel slope $\beta_a$, the following equation is derived from equation (10):

$$I = I_{ELP}\exp(2.3/\beta_a)\eta(t)) \quad (17)$$

Suppose charge $q_{\beta a}$, which satisfies equation (17), is applied to the test piece 2 at the electroless deposition potential $E_{ELP}$ and that the polarization potential of the test piece 2 arises to $\eta_m$. Then, the polarization potential varies as time elapses. A specific polarization potential $\eta_i$ is selected, which is represented as: $0 << \eta_i < \eta_m$. When the polarization potential varies to $\eta_i$, the time count is started again. If the differential capacitance $C_D$ remains constant over the period of time t in which the polarization potential varies from $\eta_i$ to $\eta_{\beta a}(t)$, then the charge consumed during the period $\Delta q_{\beta a}$ can be represented as follows:

$$\Delta q_{\beta a} = C_D(\eta_i - \eta_{\beta a}(t)) \quad (18)$$

Faradaic current density I in equation (17) corresponds to the current which has flown during the electroless plating reaction. Thus, if this current I is integrated over time t, the consumed charge $q_a$ is equal to the integrated value of the current I. That is:

$$\Delta q_{\beta a} = \int_0^t I dt = \int_0^t I_{ELP}\cdot\exp\left(\frac{2.3}{\beta_a}\eta_{\beta a}(t)\right) dt \quad (19)$$

Equations (18) and (19) are differentiated into the following equation:

$$-C_D(d\eta_{\beta a}(t)/dt)=I_{ELP}\exp(2.3/\beta_a)\eta_{\beta a}(t)) \quad (20)$$

Differential equation (20) is solved, under the initial condition of $\eta_{\beta a}(t)=\eta_i$ at $t=0$. Then, the following equation is obtained:

$$\exp\left(-\frac{2.3}{\beta_a}\eta_{\beta a}(t)\right) = \frac{I_{ELP}}{C_D}t \times \frac{2.3}{\beta_a} + \exp\left(-\frac{2.3}{\beta_a}\eta_i\right) \quad (21)$$

Figure 5:
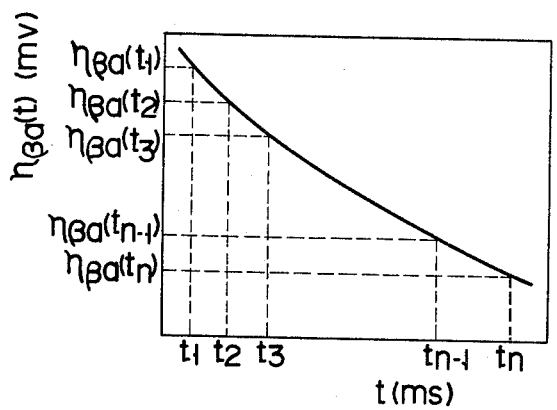
FIG. 5 is a graph showing the relationship between a lapse of time t and a polarization potential $\eta_R(t)$.

If three polarization potentials $\eta_{\beta a}(t_1)$, $\eta_{\beta a}(t_2)$ and $\eta_{\beta a}(t_3)$ of the test piece 2 at different times $t_1$, $t_2$ and $t_3$ are read from the $\eta_{\beta a}(t)-t$ curve in FIG. 5, the following three equations are established:

$$\exp\left(-\frac{2.3}{\beta_a}\eta_{\beta a}(t_1)\right) = \frac{I_{ELP}}{C_D} \times \frac{2.3}{\beta_a} t_1 + \exp\left(-\frac{2.3}{\beta_a}\eta_i\right) \quad (22)$$

$$\exp\left(-\frac{2.3}{\beta_a}\eta_{\beta a}(t_2)\right) = \frac{I_{ELP}}{C_D} \times \frac{2.3}{\beta_a} t_2 + \exp\left(-\frac{2.3}{\beta_a}\eta_i\right) \quad (23)$$

-continued $$\exp\left(-\frac{2.3}{\beta_a}\eta_{\beta a}(t_3)\right) = \frac{I_{ELP}}{C_D} \times \frac{2.3}{\beta_a} t_3 + \exp\left(-\frac{2.3}{\beta_a}\eta_i\right) \quad (24)$$

Subtracting equation (23) from equation (22), the following equation is established:

$$\exp\left(-\frac{2.3}{\beta_a}\eta_{\beta a}(t_1)\right) - \exp\left(-\frac{2.3}{\beta_a}\eta_{\beta a}(t_2)\right) = \frac{I_{ELP}}{C_D} \cdot \frac{2.3}{\beta_a}(t_1-t_2) \quad (25)$$

Subtracting the equation (24) from the equation (23), the following equation is established:

$$\exp\left(-\frac{2.3}{\beta_a}\eta_{\beta a}(t_2)\right) - \exp\left(-\frac{2.3}{\beta_a}\eta_{\beta a}(t_3)\right) = \frac{I_{ELP}}{C_D} \cdot \frac{2.3}{\beta_a}(t_2-t_3) \quad (26)$$

If the equation (25) is divided by the equation (26), the result is as follows:

$$\frac{\exp\left(-\frac{2.3}{\beta_a}\eta_{\beta a}(t_1)\right) - \exp\left(-\frac{2.3}{\beta_a}\eta_{\beta a}(t_2)\right)}{\exp\left(-\frac{2.3}{\beta_a}\eta_{\beta a}(t_2)\right) - \exp\left(-\frac{2.3}{\beta_a}\eta_{\beta a}(t_3)\right)} = \frac{t_1-t_2}{t_2-t_3} \quad (27)$$

Equation (27) shows that Tafel Slope $\beta_a$ of anodic reaction can be obtained if the polarization potential $\eta_{\beta a}(t_1)$, $\eta_{\beta a}(t_2)$ and $\eta_{\beta a}(t_3)$ at three different times $t_1$, $t_2$ and $t_3$ are read. Suppose $\eta_{\beta a}(t_1) > \eta_{\beta a}(t_2) > \eta_{\beta a}(t_3)$, $\eta_{\beta a}(t_1) = \eta_{\beta a}(t_2) + \Delta\eta_{\beta a}$ and $\eta_{\beta a}(t_3) = \eta_{\beta a}(t_2) - \Delta\eta_{\beta a}$ ($\Delta\eta_{\beta a} > 0$) and that $\Delta\eta_{\beta a}$ is therefore equal to $\eta_{\beta a}(t_1) - \eta_{\beta a}(t_2)$ and $\eta_{\beta a}(t_2) - \eta_{\beta a}(t_3)$. Then, the left term of equation (27) can be simplified as follows:

(THE LEFT TERM)

$$= \frac{\exp\left\{-\frac{2.3}{\beta_a}(\eta_{\beta a}(t_2) + \Delta\eta_{\beta a})\right\} - \exp\left(-\frac{2.3}{\beta_a}\eta_{\beta a}(t_2)\right)}{\exp\left(-\frac{2.3}{\beta_a}\eta_{\beta a}(t_2)\right) - \exp\left\{-\frac{2.3}{\beta_a}(\eta_{\beta a}(t_2) - \Delta\eta_{\beta a})\right\}}$$

$$= \frac{\exp\left(-\frac{2.3}{\beta_a}\eta_{\beta a}(t_2)\right)\left\{\exp\left(-\frac{2.3}{\beta_a}\Delta\eta_{\beta a}\right) - 1\right\}}{\exp\left(-\frac{2.3}{\beta_a}(\eta_{\beta a}(t_2) - \Delta\eta_{\beta a})\right)\left\{\exp\left(-\frac{2.3}{\beta_a}\Delta\eta_{\beta a}\right) - 1\right\}}$$

$$= \frac{\exp\left(-\frac{2.3}{\beta_a}\eta_{\beta a}(t_2)\right)}{\exp\left(-\frac{2.3}{\beta_a}\eta_{\beta a}(t_2)\right) \cdot \exp\left(\frac{2.3}{\beta_a}\Delta\eta_{\beta a}\right)}$$

$$= \frac{1}{\exp\left(\frac{2.3}{\beta_a}\Delta\eta_{\beta a}\right)}$$

Consequently, $$\frac{1}{\exp\left(\frac{2.3}{\beta_a}\Delta\eta_{\beta a}\right)} = \frac{t_1-t_2}{t_2-t_3},$$

$$\beta_a = \frac{\Delta\eta_{\beta a}}{\log\frac{t_3-t_2}{t_1-t_2}} \quad (28)$$

Equation (28) shows that anodic Tafel slope $\beta_a$ can be easily calculated by reading from the $\eta_{\beta a}(t)$-t curve $\eta_{\beta a}(t) >> 0$ the time $t_2$ at which the potential $\eta_{\beta a}(t_2)$ is recorded, the time $t_1$ at which the potential $\eta_{\beta a}(t_1)$ higher than $\eta_{\beta a}(t_2)$ by $\Delta\eta_{\beta a}$ is recorded and the time $t_3$ is at which the potential $\eta_{\beta a}(t_3)$ lower than $\eta_{\beta a}(t_2)$ by $\Delta\eta_{\beta a}$ is recorded. In other words, Tafel slope $\beta_a$ is calculated based on only $\Delta\eta_{\beta a}$, $t_1$, $t_2$ and $t_3$.

In practice, Tafel slope $\beta_a$ is calculated accurately in the following way.

Suppose such a $\eta_{\beta a}(t)$-t curve as shown in FIG. 5 is obtained, wherein $\eta_{\beta a}(t)$ is more than 50 millivolts. Polarization potentials $\eta_{\beta a}(t_1)$, $\eta_{\beta a}(t_2)$, $\eta_{\beta a}(t_3)$ ..., $\eta_{\beta a}(t_{n-1})$ and $\eta_{\beta a}(t_n)$ are selected from the curve, where $\eta_{\beta a}(t_1) - \eta_{\beta a}(t_2) = \eta_{\beta a}(t^2) - \eta_{\beta a}(t_3) = \ldots = \eta_{\beta a}(t_{n-1}) - \eta_{\beta a}(t_n) = \Delta\eta_{\beta a}$, the corresponding times $t_1, t_2, t_3, \ldots, t_{n-1}$ and $t_n$ are read off the time axia. The times are combined to form a first group $(t_1, t_2, t_3)$, a second group $(t_2, t_3, t_4), \ldots$, and the last group $(t_{n-2}, t_{n-1}, t_n)$. From these groups the following items are calculated:

$$\frac{t_3-t_2}{t_2-t_1}, \frac{t_4-t_3}{t_3-t_2}, \ldots \frac{t_n-t_{n-1}}{t_{n-1}-t_{n-2}}$$

The average $\delta$ of these items calculated as follows:

$$\delta = \frac{1}{n-2}\left(\frac{t_3-t_2}{t_2-t_1} + \frac{t_4-t_3}{t_3-t_2} + \ldots \frac{t_n-t_{n-1}}{t_{n-1}-t_{n-2}}\right) \quad (29)$$

Equation (28) is rewritten into the following equation using the average $\delta$;

$$\beta_a = \Delta\eta_{\beta a}/\log\delta \quad (30)$$

In this way anodic Tafel slope $\beta_a$ can be obtained accurately.

In equations (26), (27) and (30) there are no terms including $I_{ELP}$ or $C_D$. Thus Tafel slope $\beta_a$ can be easily analyzed from these equations. But, if $\Delta\eta_{\beta a}$ (i.e. difference between $\eta_{\beta a}(t_1)$ and $\eta_{\beta a}(t_2)$, between $\eta_{\beta a}(t_2)$ and $\eta_{\beta a}(t_3)$ and so forth) is set to be relatively large, the differential capacitance $C_D$ may inevitably vary. $\Delta\eta_{\beta a}$ should therefore be made sufficiently small, for instance 10 millivolts or less, so that the variation of instance 10 millivolts or less, so that the variation of $C_D$ is negligible small, and $C_D$ is considered to be constant.

In order to obtain cathodic Tafel slope $\beta_c$ of cathodic reaction, the polarization potential $\eta_{\beta c}(t)$ is changed to not more than $-30$ millivolts, preferably $-60$ to $-50$ millivolts or lower. Then the following equation will be established:

$$I = -I_{ELP}\exp(-(2.3)/(\beta_c)\eta_{\beta c}(t)) \quad (31)$$

Equation (31) is similar to equation (17). Thus, similar equations to equations (18), (19) and (20) are established. And the following equation, which is similar to equation (21), is also established:

$$\exp\left(\frac{2.3}{\beta_c}\eta_{\beta c}(t)\right) = \frac{I_{ELP}}{C_D} t \times \frac{2.3}{\beta_c} + \exp\left(\frac{2.3}{\beta_c}\eta_i\right) \quad (32)$$

Polarization potentials $\eta_{\beta c}(t_1)$, $\eta_{\beta c}(t_2)$ and $\eta_{\beta c}(t_3)$ at three different times $t_1$, $t_2$ and $t_3$ are read from the $\eta_{\beta c}(t)-t$ curve obtained by lowering $\eta_{\beta c}(t)$ to $-60$ to $-50$ millivolts or lower. If $\eta_{\beta c}(t_1) < \eta_{\beta c}(t_2) < \eta_{\beta c}(t_3)$ and $\eta_{\beta c}(t_1) = \eta_{\beta c}(t_2) - \Delta\eta_{\beta c}$, $\eta_{\beta c}(t_2) = \eta_{\beta c}(t_3) - \Delta\eta_{\beta c}(\Delta\eta_{\beta c} > 0)$, then Tafel slope $\beta_c$ can be expressed as follows:

$$\beta_c = \frac{\Delta\eta_{\beta c}}{\log\frac{t_3 - t_2}{t_2 - t_1}} \quad (33)$$

If many polarization potentials $\eta_{\beta c}(t_1)$, $\eta_{\beta c}(t_2)$, $\eta_{\beta c}(t_3)$ ... $\eta_{\beta c}(t_{n-1})$ and $\eta_{\beta c}(t_n)$ are selected from the $\eta_{\beta c}(t)-t$ curve where $\eta_{\beta c}(t_2) - \eta_{\beta c}(t_1) = \eta_{\beta c}(t_3) - \eta_{\beta c}(t_2) = \ldots = \eta_{\beta c}(t_n) - \eta_{\beta c}(t_{n-1}) = \Delta\eta_{\beta c}$, thereby reading out the corresponding times $t_1$, $t_2$, $t_3$, ... $t_{n-1}$ and $t_n$, equations similar to equations (29) and (30) will be established. That is, cathodic Tafel slope $\beta_c$ is expressed as follows:

$$\beta_c = \Delta\eta_{\beta c}/\log \delta \quad (34)$$

In equation (34) average $\delta$ is expressed as follows:

$$\delta = \frac{1}{n-2}\left(\frac{t_3 - t_2}{t_2 - t_1} + \frac{t_4 - t_3}{t_3 - t_2} + \ldots + \frac{t_n - t_{n-1}}{t_{n-1} - t_{n-2}}\right) \quad (35)$$

Now that the reaction resistance $R_{ELP}$ anodic Tafel slope $\beta_a$ and cathodic Tafel slope $\beta_c$ have been obtained in the forementioned manner, the electroless plating current density $I_{ELP}$ can be calculated by equation (1): $I_{ELP} = (K/2.3)R_{ELP}$, wherein $K = \beta_a\beta_c/(\beta_a\beta_c)$. The electroless plating current density $I_{ELP}$ is substituted in equation (2): $V_{ELP} = (M/n \cdot F)I_{ELP}$ so that the rate of electroless plating $V_{ELP}$ of the test piece 2 is calculated.

The quantity of electricity $Q_{ELP}$ consumed by the electroless plating is obtained as expressed by equation (3). Further, the weight $W_{ELP}$ of metal deposited is obtained as shown in equation (4). The surface condition of the metal layer deposited and the condition of the plating bath can be evaluated in accordance with a variation of the differential capacitance $C_D$ as shown in equation (9). Further, the adhesion of the metal layer deposited on the metal piece 2 can be evaluated according to a variation of the reaction resistance $R_{ELP}$ which is read from the log $\eta_R(t)-t$ curve which in turn is obtained from equation (8).

As mentioned above, it is possible with the method according to this invention to obtain a reaction resistance $R_{ELP}$ and Tafel slopes $\beta_a$ and $\beta_c$. If the variation of Tafel slopes $\beta_a$ and $\beta_c$ which occurs during the electroless plating is negligibly small, Tafel slopes $\beta_a$ and $\beta_c$ may be regarded as constants, and the rate of plating $V_{ELP}$ may be obtained based only on the reaction resistance $R_{ELP}$.

The apparatus shown in FIG. 1 is a three-electrode type. It has three electrodes, i.e. the test piece 2 (working electrode), the counter electrode 6 and the reference electrode 8. This three-electrode type apparatus may be replaced by such a two-electrode type as illustrated in FIG. 6.

Figure 6:
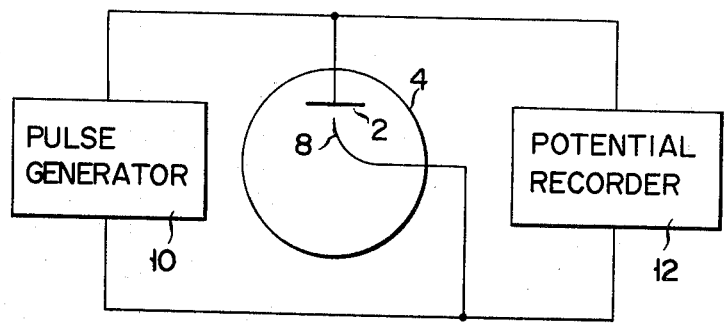
FIG. 6 is a block diagram of an apparatus of two-electrode type.

The apparatus shown in FIG. 6 comprises a test piece (or working electrode) 2 and a reference electrode 8 which acts as a counter electrode for supplying charge to the test piece 2, too. Of course, the reference electrode 8 functions to detect the polarization potential of the test piece 2. The reference electrode 8 should keep its potential constant during measurement. Between the test piece 2 and the reference electrode 8 a pulse generator 10 and a potential recorder 12 are connected as shown in FIG. 6.

If the test piece 2 and the electrode 8 of the apparatus shown in FIG. 6 are made of the same material, electroless plating reaction takes place on the reference electrode 8 in the same manner as the test piece 2. In this case, the potential recorder 12 detects the difference in polarization potential between the test piece 2 and the reference electrode 8. Thus, equation (9) cannot apply, and the following equation (36) applies in this case.

It will be now explained how to obtain the reaction resistance $R_{ELP}$ based on the recorded potential difference $\phi(0)$ between the first and second test pieces 2, 8.

Extrapolation is applied as mentioned above, thereby obtaining an initial potential difference $\delta_0$ from the recorded value. Then, a differential capacitance $C_D$ is arrived at by the following equation (36) which resembles equation (9):

$$\phi(0) = q_R/C_D(1/S_1 + 1/S_2) \quad (36)$$

Here, $S_1$ denotes the area of the first test metal piece 2, and $S_2$ the area of the second test metal piece 8. Based on the differential capacitance $C_D$ and the inclination $(-1/C_D R_{ELP})$ of the line n the logarithmic graph which serves the extrapolation, the reaction resistance $R_{ELP}$ can be obtained.

Equation (36) is formulated in the following way. The charge $q_1$ between the solution and the electrical double layer of the first test piece 2 has the opposite polarity to the charge $q_2$ between the solution and the electrical double layer of the second test piece 8. Both charge $q_1$ and $q_2$ are of the same absolute value. Thus, the surface charge density $\Delta q_1$ of the first piece 2 and the surface charge density $\Delta q_2$ of the second piece 64 are represented by the following equations (37) and (38), respectively:

$$\Delta q_1 = q/S_1 \quad (37)$$

$$\Delta q_2 = -q/S_2 \quad (37)$$

As explained with reference to equation (7), the time-based change of polarization potential $\phi_1(t)$ due to the electroless plating reaction on the first test metal piece 2 and the time-based change of polarization potential $\phi_2(t)$ due to the electroless plating reaction on the second test metal piece 8 are expressed by the following equations (38) and (39), respectively:

$$\phi_1(t) = \phi_1(0)\exp(-t/C_D R_{ELP}) \quad (38)$$

$$\phi_2(t) = \phi_2(0)\exp(-t/C_D R_{ELP}) \quad (39)$$

In equations (38) and (39), $\phi_1(0)$ denotes the initial polarization potential of the first test piece 2, and $\phi_2(0)$ the initial polarization potential of the second test piece 8. In theory, these initial polarization potentials can be represented by the following equations:

$$\phi_1(0) = \Delta q_1/C_D = q/S_1 C_D \quad (40)$$

$$\phi_2(0) = \Delta q_2/C_D = -q/S_2 C_D \quad (41)$$

Consequently, equations (38) and (39) are transformed as follows:

$$\phi_1(t) = (q/S_1 C_D) \exp(-t/C_D R_{ELP}) \quad (41)$$

$$\phi_2(t) = (-q/S_2 C_D) \exp(-t/C_D R_{ELP}) \quad (42)$$

Since the difference between $\phi_1(t)$ and $\phi_2(t)$ is recorded by the potential recorder 12, the potential difference $\phi(t)$ recorded by the recorder 12 is expressed as follows:

$$\phi(t) = \phi_1(t) - \phi_2(t) = q/C_D(1/S_1 + 1/S_2) \exp(-t/C_D R_{ELP}) \quad (43)$$

Here, equation (43) is transformed into equation (36):

$$\phi(0) = q/C_D(1/S_1 + 1/S_2) \quad (36)$$

If $S_1$ and $S_2$ are equal, that is $S_1 = S_2 = S$, equation (36) is transformed into equation (44):

$$C_D = \Delta q/2\phi(0) \quad (44)$$

Thus, differential capacitance $C_D$ can easily be obtained by equation (36) or (44), just as easily as by equation (9).

Figure 7:
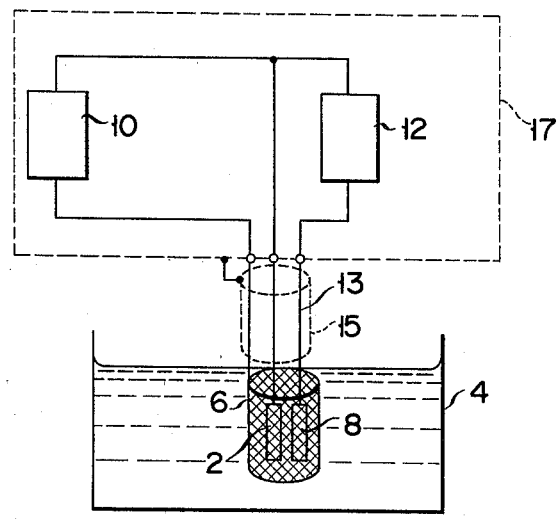
FIGS. 7 and 8 show block diagrams of arrangement of electrodes according to this invention.

Moreover, according to this invention, the electrodes of the apparatus should better be arranged as shown in FIG. 7. An electroless plating bath is generally stirred by means of an air blower so that it is made stable enough to form a metal layer of a uniform thickness. When the plating bath is stirred, however, it flows along unsteady courses. Such random flow of liquid would in some case create noise in the measured potential. Further, as shown in FIG. 7, the test piece 2 and the reference electrode 8 are connected to the potential recorder 12 by wires. If these wires are not electrically shielded, the noise is likely to sneak into the measured potential through the wires. The noise thus reduce the accuracy of the measurement.

To make the measured value free from such noise, a hollow cylinder which is made of a net or which has many apertures is used as a counter electrode 6, and the test piece 2 and the reference electrode 8 are disposed within the counter electrode 6. The counter electrode 6 protects the test piece 2 and the electrode 8 against a random flow of plating bath. Further, wires 13 which connect the test piece 2, the counter electrode 6 and the reference electrode 8 to the pulse generator 10 and the potential recorder 12 extend through a shield sheath 15, which is attached to a shield case 17 shielding the pulse generator 10 and the potential difference recorder 12.

Since the test piece 2 and the reference electrode 8 are disposed in the hollow cylindrical counter electrode 6, the noise created by the stirring of the plating bath and that induced by AC lines are prohibited from reaching the test piece 2 and the reference electrode 8. Further, since the wires 13 are protected by the shield sheath 15, the noise is prevented from reaching the potential difference recorder 12. As a result, the accuracy of measurement will be enhanced.

Figure 8:
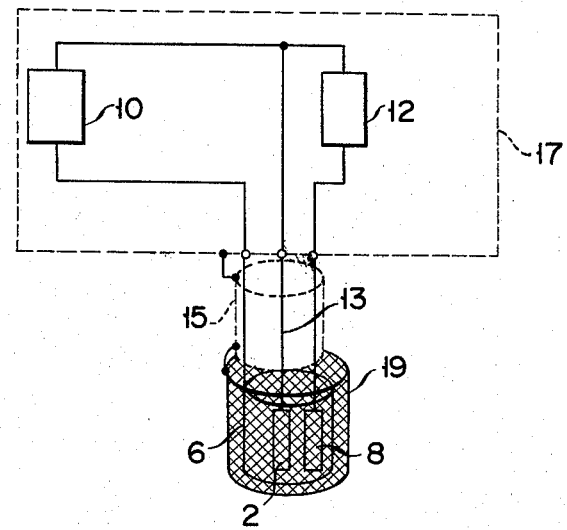

To further enhance the accuracy of measurement, the hollow cylindrical counter electrode 6 may be disposed within a hollow cylindrical shield electrode 19 which is made of a net or which has many apertures, as illustrated in FIG. 8. It is preferred that the shield electrode 19 should be connected to the shield sheath 15. It is also preferred that the shield electrode 19 should be made of the same material as the counter electrode 6. Of course, it is sufficient if the electrodes 6 and 19 are made of such material as is electrically conductive and as would not emit ions in the plating bath to impede the electroless plating reaction. Further, the shield electrode 19 may be coated with a resin, glass or the like so that a metal may not be deposited on it.

With reference to FIGS. 9 to 12, various apparatus for carrying out the method of this invention for measuring the rate of electroless plating will be described more in detail.

Figure 9:
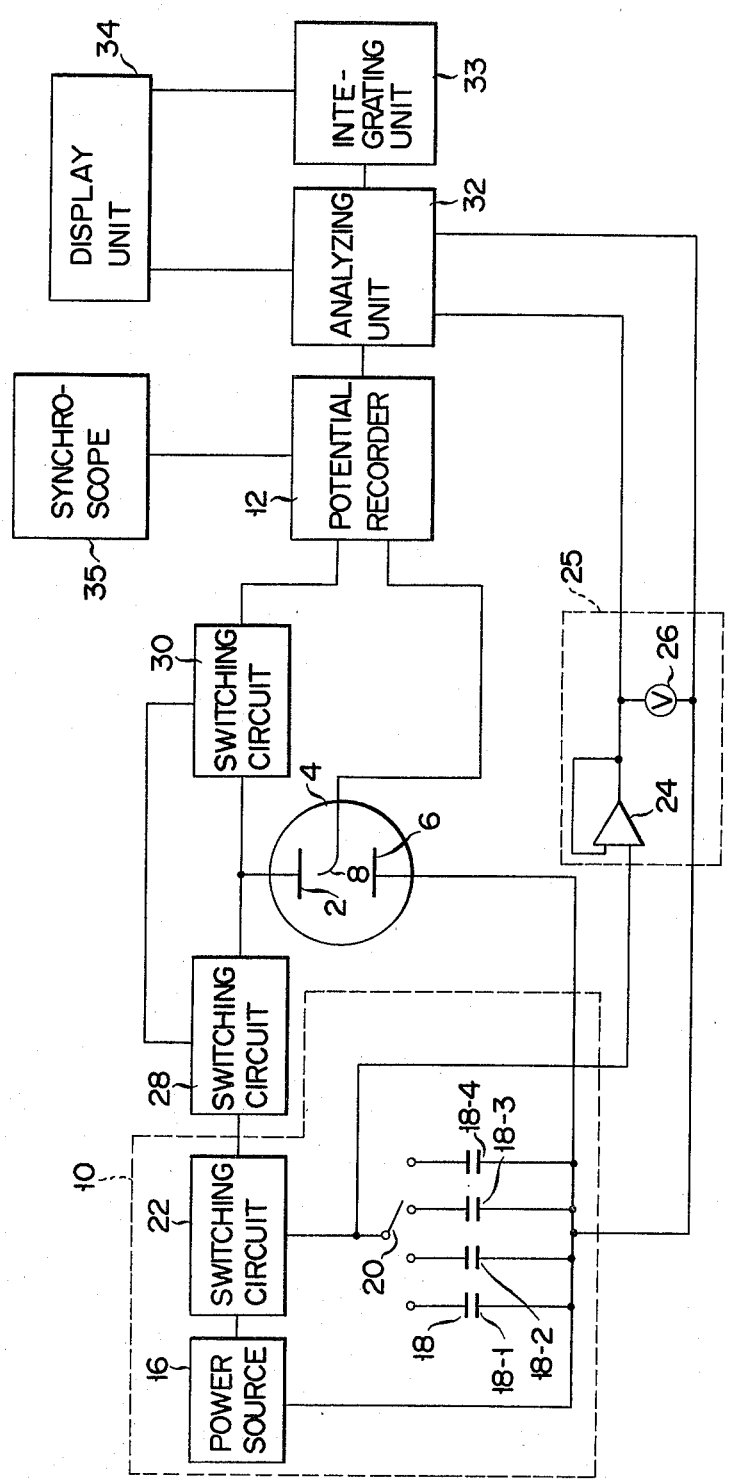
FIGS. 9 to 12 are circuit diagrams each illustrating an apparatus for carrying out a method of evaluating electroless plating according to this invention.

The apparatus shown in FIG. 9 comprises a metal test piece 2, a cell 4 filled with test liquid, a counter electrode 6, a reference electrode 8, a pulse generator 10 and a potential recorder 12. The potential recorder 12 may include a bias voltage source (not shown) which applies a bias voltage to the detected potential, thereby to detect only the variation of polarization potential $\eta(t)$. In other words, the bias voltage source cancels out the electroless deposition potential from the output signal of the potential recorder 12.

The pulse generator 10 is constituted by a power source 16, four capacitors 18-1 to 18-4 for accumulating charge from the power source 16, a rotary switch 20 for selecting one of the capacitors and a first switching circuit 22 for instantaneously applying charge from the selected capacitor to the metal test piece 2. The capacitors 18-1 to 18-4 have different capacitances $C_1$ to $C_4$, respectively. One end of each capacitors is connected to the corresponding fixed contact of the rotary switch 20, and the other end to the power source 16 and the counter electrode 6. The movable contact of the switch 20 is connected to the power source 16 through the first switching circuit 22.

The capacitors 18-1 to 18-4 and the rotary switch 20 constitute a series circuit. The pulse generator 10 is provided with a voltage measuring unit 25. The voltage measuring unit 25 is comprised of an operational amplifier 24 and a voltmeter 26, which are connected in series. This unit 25 is connected in parallel to the series circuit of the capacitors 18-1 to 18-4 and the rotary switch 20.

The first switching circuit 22 connects the selected capacitor to the power source 16 so that the capacitor is charged. It connects any one of the capacitors 18-1 to 18-4 between the metal test piece 2 and the counter electrode 6 so that the electrical double layer of the test piece 2 is charged. As will be described later, the first switching circuit 22 is constituted by a timer and a relay.

The measuring apparatus of FIG. 9 further comprises a second switching circuit 28 and a third switching circuit 30. The second switching circuit 28 is connected between the test piece 2 and the first switching circuit 22. The second switching circuit 28 disconnects the test piece 2 from the first switching circuit 22 upon completion of the necessary charge supply from the selected capacitor to the test piece 2 through the first switching circuit 22. Thus, the second switching circuit 28 is provided for detecting an accurated polarization potential of the test piece 2. That is, without the circuit 28, the selected capacitor would keep applying charge to the test piece 2 even while the recorder 12 is detecting the polarization potential of the test piece 2. As result, the recorder 12 would unnecessarily detect an ohmic drop. If the detected potential of the test piece 2 contains an ohmic drop, it is impossible to obtain a correct $\eta(t)-t$ curve.

In other words, the second switching circuit 28 opens upon lapse of a specific period of time from the start of charge supply to the test piece 2, thereby stopping the charge supply. Thus, the reference electrode 8 can detect exclusively the varying potential $\eta(t)$ of the test piece 2, never an ohmic drop after the circuit 28 has opened. Consequently, a correct $\eta(t)-t$ curve containing no error due to the solution resistance $R_s$ etc. is obtained. Said specific period is so long as to apply charge the test piece 2 to the predetermined polarization potential $\eta(t)$ of $-30$ to 30 millivolts, preferably $-10$ to 10 millivolts, in order to obtain the reaction resistance $R_{ELP}$, which is 30 millivolts or more, preferably 50 millivolts or more in order to obtain Tafel slope $\beta_a$ and which is $-30$ millivolts or less, preferably $-50$ millivolts or less in order to obtain Tafel slope $\beta_c$. If the solution resistance $R_s$ is not so high, the second switching circuit 28 is unnecessary. The third switching circuit 30 is required particularly when one of the capacitors 18-1 to 18-4 which is connected to the test piece 2 and the counter electrode 6 can be charged to a voltage higher than the maximum voltage which the potential recorder 12 can measure. Thus, the third switching circuit 30 is unnecessary if the potential recorder 12 can measure a sufficiently high voltage.

To the potential recorder 12, a data analyzing unit 32, is connected. To the data analyzing unit 32 the voltmeter 26 of the voltage measuring unit 25 is connected. The data analyzing unit 32 analyzes the charge $q_R$ applied to the test piece 2, initial polarization potential $\eta(0)$ and differential capacitance $C_D$ in accordance with the capacitance of the selected capacitor, the potential change of the selected capacitor which has been detected by the voltmeter 26 and the change of polarization potential $\eta(t)$ which has been detected by the recorder 12.

The unit 32 calculates the reaction resistance $R_{ELP}$ and Tafel slopes $\beta_a$ and $\beta_c$. Further, it calculates the electroless plating current density $I_{ELP}$. The unit 32 is connected to an integrating circuit 33. The integrating circuit 33 integrates the electroless plating current density $I_{ELP}$, using a time parameter, thus obtaining the weight $W_{ELP}$ of the metal deposited on the test piece 2.

To the potential recorder 12 and the integrating circuit 33 there is connected a display unit 34 which can display the initial polarization potential $\eta(0)$, the differential capacitance $C_D$, the reaction resistance $R_{ELP}$, Tafel slopes $\beta_a$ and $\beta_c$, the electroless plating current density $I_{ELP}$, plating weight $W_{ELP}$, plating rate $V_{ELP}$ and so on. Further, a synchroscope 35 is connected to the potential recorder 12. The synchroscope 35 can monitor the curve which shows the relationship between time and the polarization potential $\eta(t)$ measured by the recorder 12.

Figure 10:
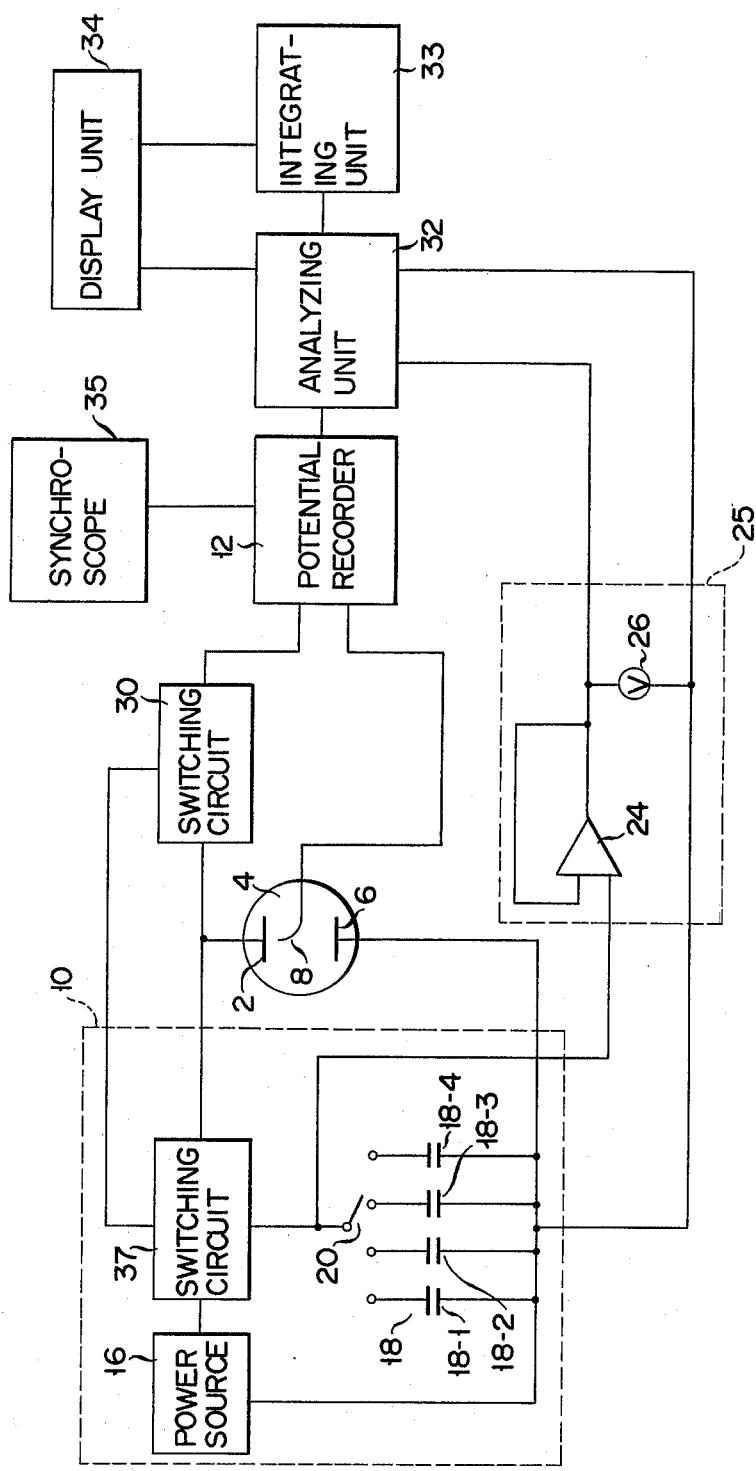

The measuring apparatus shown in FIG. 10 differs from the apparatus of FIG. 9 only in that a single switching circuit 37 is provided in place of the first switching circuit 22 and the second switching circuit 28. The switching circuit 37 connects the selected capacitor to the power source 16 so that the capacitor is charged. It connects the selected capacitor between the test piece 2 and the counter electrode 6 so that the charge is applied from the capacitor to the test piece 2. It disconnects the selected capacitor from the test piece 2 while the polarization potential of the test piece 2 is detected.

Figure 11:
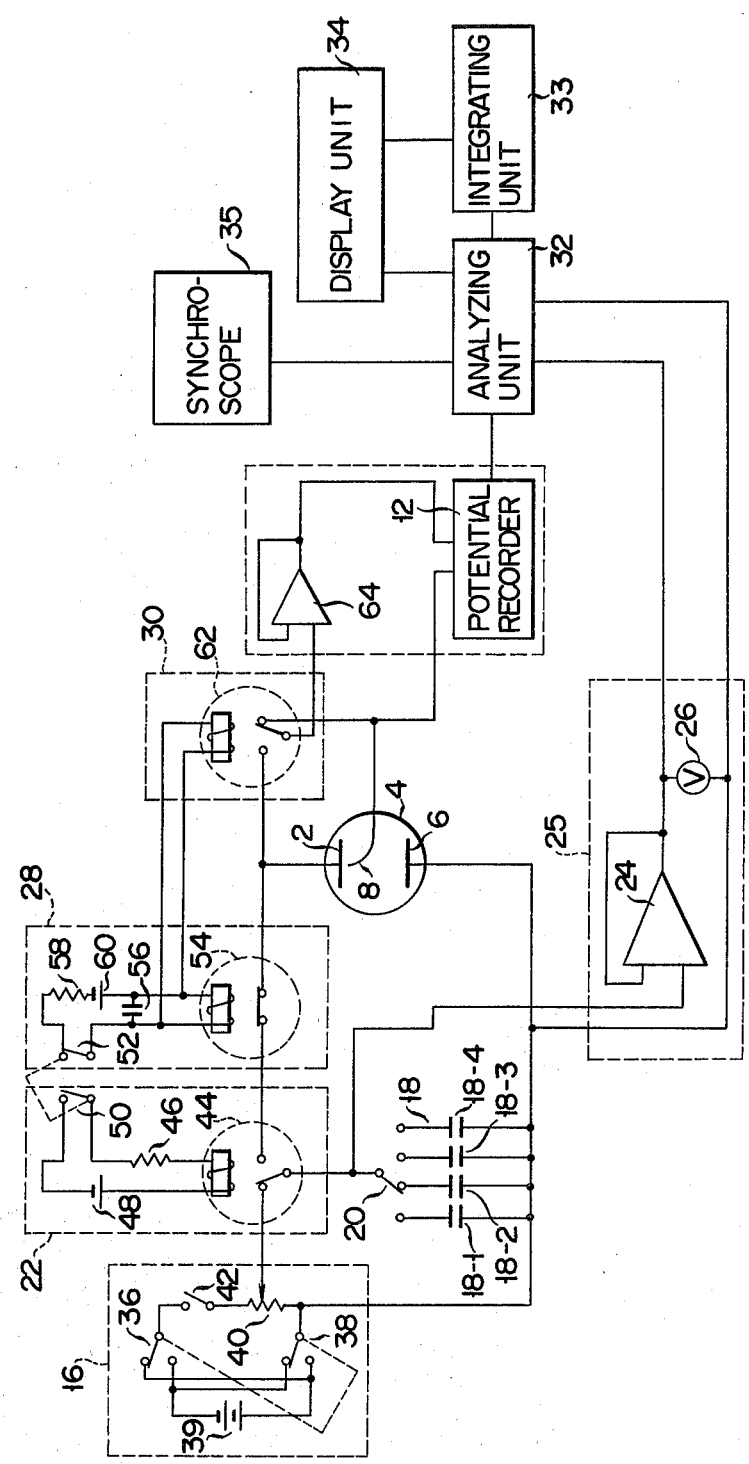

The measuring apparatus shown in FIG. 9 is more fully illustrated in FIG. 11. As shown in FIG. 9, the power source 16 is constituted by a battery 39, a pair of polarity changeover switches 36 and 38 ganged to each other, a variable resistor 40 and a switch 42. The variable resistor 40 and the switch 42 form a series circuit, which is connected between the movable contacts of the polarity changeover switches 36 and 38. The polarity changeover switches 36 and 38 are so connected to the battery 39 as to apply a positive charge or a negative charge to the test piece 2, thereby obtaining Tafel slope $\beta_a$ of the anodic reaction of the test piece 2 and Tafel slope $\beta_c$ of cathodic reaction of the test piece 2 and also obtaining reaction resistance $R_{ELP}$, if necessary. The variable resistor 40 is provided to control the voltage applied to the selected capacitor.

The first switching circuit 22 is constituted by a relay 44, a resistor 46, a battery 48 and a starting switch 50 for energizing the relay 44. The relay 44 has a first fixed contact connected to the movable contact of the variable resistor 40, a second fixed contact is connected to the test piece through the second switching circuit 28 and a movable contact connected to the rotary switch 20. The movable contact of the relay 44 is normally in contact with the first fixed contact and is brought into contact with the second fixed contact when the relay 44 is energized.

The second switching circuit 28 is constituted by a relay 54, a start switch 52 connected to the relay 54, a capacitor 56 connected in parallel to the series connected starting switch 52, a resistor 58, and a battery 60. The relay 54 has a normally closed contact connected between the test piece 2 and the second fixed contact of the relay 44. The start switch 52 is ganged with the start switch 50 of the first switching circuit 22.

The third switching circuit 30, which is connected between the test piece 2 and the potential difference recorder 12, is constituted by a relay 62 which is connected in parallel to the capacitor 56 of the second switching circuit 28. The relay 62 has a first fixed contact connected to the test piece 2, a movable contact and a second fixed contact connected to the reference electrode 8. The potential recorder 12 is provided with an operational amplifier 64 which acts as a voltage follower. The movable contact of the relay 62 is connected to the operational amplifier 64 and is normally in contact with the second fixed contact and is put into contact with the first fixed contact when the relay 62 is energized. The operational amplifier 64 is connected to the recorder 12. Another operational amplifier 66 is connected between the voltmeter 26 and the switch 24.

It will now be described how the measuring apparatus shown in FIG. 9 operates. First, the switch 20 is operated to select one of the capacitors 18-1 to 18-4. Which capacitor is selected depends on which is to be obtained the reaction resistance $R_{ELP}$ of the test piece 2, Tafel slope $\beta_a$ of anodic reaction, or Tafel slope $\beta_c$ of cathodic reaction. The selection of capacitor also depends on the material and the surface area S of the test piece 2 and the properties of the bath. Then, the polarity changeover switches 36 and 38 are set to apply a positive or negative charge to the test piece 2. This done, the movable contact of the variable resistor 40 is so moved as to apply a specific voltage on the selected capacitor. Thereafter, the switch 42 is closed to charge the selected capacitor.

The voltmeter 26 measures the voltage applied on the selected capacitor, and the voltage change of the selected capacitor is supplied to the data analyzing unit 32. Both start switches 50 and 52 are closed to start supplying charge to the electrical double layer of the test piece 2. Upon a lapse of time, which is determined by the resistance of a resistor 58 and the capacitance of a capacitor 56, a relay 54 is energized to open its normally closed contact. At the same time, a relay 62 is energized to have its movable contact brought into contact with its first fixed contact. As a result, the charge supply to the test piece 2 is stopped, and the potential recorder 12 starts recording the decay of the polarization potential $\eta(t)$ of the test piece 2. The recorded decay of the potential $\eta(t)$ is monitored by the synchroscope 34 and analyzed by the data analyzing unit 32, thereby to obtain a reaction resistance $R_{ELP}$, anodic Tafel slope $\beta_a$, cathodic Tafel slope $\beta_c$ and electroless plating current density $I_{ELP}$.

The integrating circuit 33 calculates the weight $W_{ELP}$ of the metal deposited on the test piece, based on the electroless plating current density $I_{ELP}$. The weight $W_{ELP}$ and the data obtained by the data analyzing unit 32 are displayed by the display unit 34.

Figure 12:
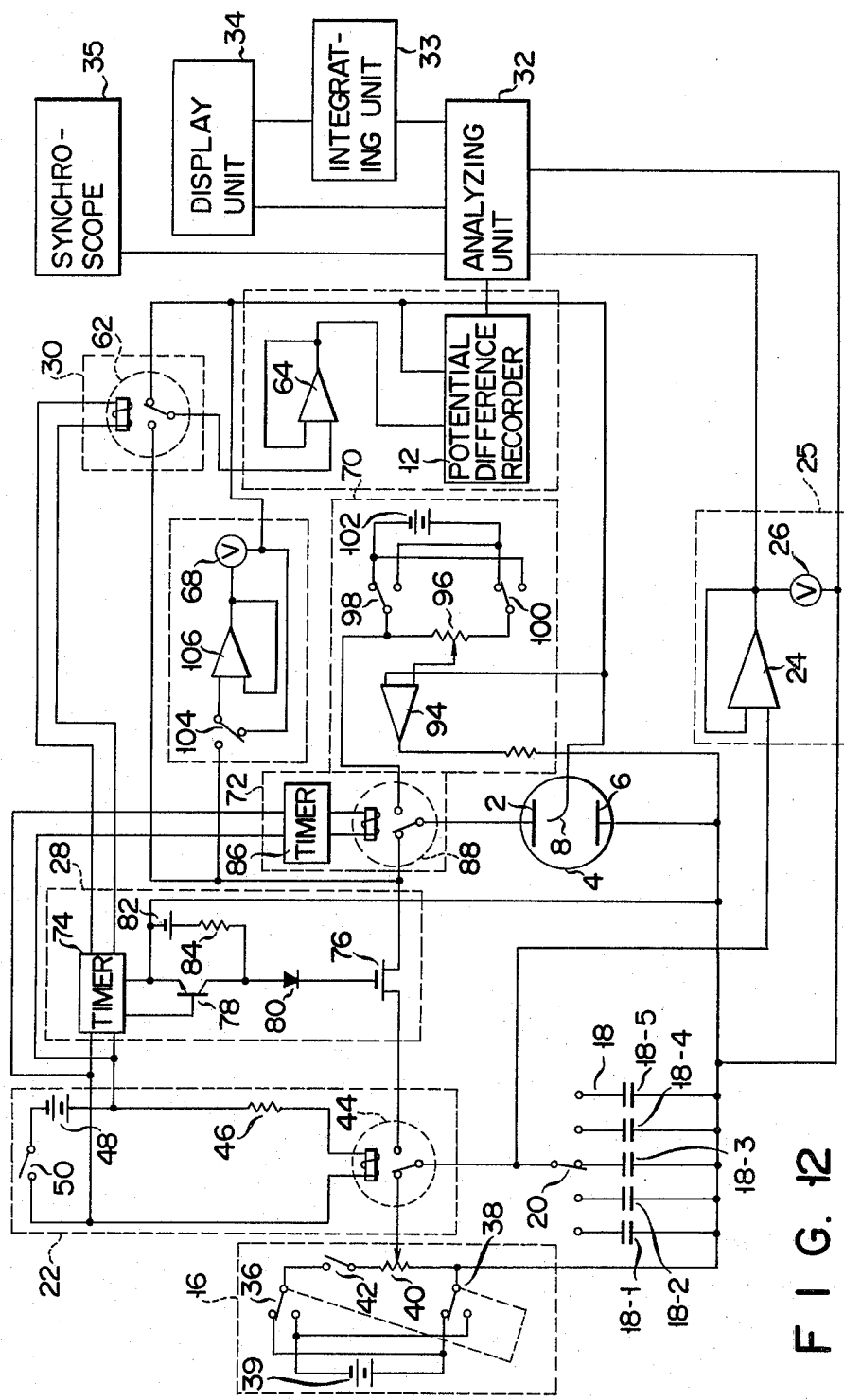

The measuring apparatus of FIG. 11 may be modified as shown in FIG. 12. The modified apparatus differs in that it is provided with a voltmeter 68 and a bias circuit 70 and its second switching circuit 28 is designed somewhat different. Voltmeter 68 is provided to detect the electroless deposition potential $E_{ELP}$ of the test piece 2, and the bias circuit 70 is provided to apply a bias voltage on the test piece 2 to forcibly bring the potential thereof back to the electroless deposition potential $E_{ELP}$ upon completion of recording of a polarization variation. The apparatus shown in FIG. 12 is further provided with a fourth switching circuit 72 for connecting the test piece 2 to the bias circuit 70.

The second switching circuit 28 of the apparatus of FIG. 10 includes a timer 74 and an FET (field effect transistor) 76. The timer is connected to a series circuit constituted by a starting switch 50 and a battery 48. The FET 76 has its source and drain connected to the second fixed contact of relay 44 and the fourth switching circuit 72, respectively. One output of the timer 74 is connected to the base and emitter of a transistor 78, the collector of which is connected to the gate of the FET 76 through diode 80. Between the emitter and collector of the transistor 78, battery 82 and resistor 84 are connected to form a series circuit. The emitter of the transistor 78 is connected to the counter electrode 6.

The fourth switching circuit 72 is constituted by a timer 86 and a relay 88. The timer 86 is connected in parallel to the series circuit of starting switch 50 and battery 48. The relay 88 is connected to the output of the timer 86. The relay 88 has a first fixed contact connected to the drain of the FET 76, a second fixed contact connected to the bias circuit 70 and a movable contact connected to the test piece 2. The movable contact of the relay 88 is kept connected to the first fixed contact so long as the relay 88 is not energized.

The output of the timer 74 of the second switching circuit 28 is connected to the relay 62 of a third switching circuit 30. The bias circuit 70 is constituted by an operational amplifier 94, variable resistor 96, a pair of polarity changeover switches 98 and 100 and a battery 102. The operational amplifier 94 acts as a voltage restricting circuit and has its output connected to the counter electrode 6 through a resistor 95. One input terminal of the operational amplifier 94 is connected to the reference electrode 8. Variable resistor 96 has its movable contact connected to the other input terminal of the operational amplifier 94. Battery 102 is connected between the polarity changeover switches 98 and 100. The potential applied to the test piece 2 by the bias circuit 70 is the difference between the polarization potential of the test piece 2 and the electroless deposition potential $E_{ELP}$ detected by the voltmeter 68. This potential is controlled by the variable resistor 96. Voltmeter 68 is connected between the reference electrode 8 and the first fixed contact of the relay 88 of the fourth switching circuit 72, through operational amplifier 106 and switch 104.

The movable contact of switch 104 is connected to the input terminal of the operational amplifier, one of the fixed contacts of the switch 104 is connected to the voltmeter and the other fixed contact is connected to the first fixed contact of relay 88.

It will now be described how the measuring apparatus shown in FIG. 12 operates. First, the switch 104 is changed over whereby the electroless deposition potential $E_{ELP}$ of the metal test piece 2 is measured by the voltmeter 68. Then, the variable resistor 96 of the bias circuit 70 is adjusted so that its movable contact may receive the same potential as the electroless deposition potential $E_{ELP}$ of the test piece 2. When the start switch 50 is closed, the relay 44 of the first switching circuit 22 is energized to bring the movable contact of the relay 44 into contact with the second fixed contact. At the same time the timer 74 is operated to turn on the transistor 78. As a result, conduction is effected between the source and drain of the FET 76, and the selected capacitor starts applying charge to the test piece 2.

Upon lapse of a predetermined time, for example, several microseconds to tens of milliseconds, the timer 74 turns off the transistor 74, whereby conduction between the source and drain of the FET 76 is no longer achieved and the relay 62 is energized. When the charge supply of charge to the test piece 2 is stopped, the movable contact of the relay 62 of the third switching circuit 30 is put into contact with the first fixed contact of the relay 62. Then, the potential recorder 12 starts recording the variation of the polarization potential $\eta(t)$.

Upon lapse of a predetermined time, the timer 86 energizes the relay 88, thereby bringing the movable contact thereof into contact with the second fixed contact thereof. Consequently, the bias current 70 applies a prescribed potential on the test piece 2, thus bringing the test piece 2 back to the electroless deposition potential $E_{ELP}$. Namely, the potential of the test piece 2 detected by the reference electrode 8 is compared with the same potential as the electroless deposition potential $E_{ELP}$ appearing at the movable contact of the variable resistor 96, and the voltage corresponding to the potential difference is applied between the counter electrode 6 and the test piece 2 by the operational amplifier 94. As a result, a charge exchange is effected between the test piece 2 and the counter electrode 6, whereby the potential of the test piece 2 is brought back to the electroless deposition potential $E_{ELP}$. After the potential of the test piece 2 has been brought to the electroless deposition potential $E_{ELP}$, a variation of the polarization potential η(t) of the test piece 2 can be recorded again.

It will now be described how the method of this invention evaluated electroless plating and what values the apparatus of this invention obtained.

In the apparatus of the above-described construction, two platinum plates each having surface area of 2 cm² were used as the working electrode 2 and the counter electrode 6, respectively. A saturated calomel electrode was used as the reference electrode 8. These electrodes 2, 6 and 8 were immersed in an electroless plating bath which had been heated to 40° C. and whose chemical composition was as follows:

| Copper sulfate | 0.03 mol/l |
|---|---|
| EDTA | 0.08 mol/l |
| Formaldehyde | 0.20 mol/l |
| pH | 12 (adjusted with sodium hydroxide) |

The electrodes 2, 6 and 8 were kept immersed in the plating bath. For the first five hours of the electroless plating, it was detected and recorded how the reaction resistance $R_{ELP}$ and Tafel slopes $\beta_a$ and $\beta_c$ varied. The results were as shown in FIG. 13, wherein curve I represents the variation of the reaction resistance $R_{ELP}$, curve II the variation of Tafel slope $\beta_a$, and curve III the variation of Tafel slope $\beta_c$.

From the data shown in FIG. 13 the electroless deposition current density $I_{ELP}$ was calculated according to equation (1). Also based on the data shown in FIG. 13 the differential capacitance $C_D$ was obtained. It was observed that the electroless deposition current density $I_{ELP}$ and the capacitance $C_D$ varied as indicated by curve IV and curve V in FIG. 14, respectively. Since the electroless deposition current density $I_{ELP}$ is proportional to the plating rate as clearly understood from equation (2), curve IV in FIG. 14 shows that the plating rate became lower as time elapses.

As shown in FIG. 14, the differential capacitance $C_D$ was at first over 250 μF/cm₂. This value is believed to be approximately equal to the differential capacitance of the platinum electrode 2. As time elapsed, more and more copper was deposited, and the differential capacitance $C_D$ grew smaller. This means that the platinum electrode 2 was covered with a copper layer to have its surface rendered increasingly smooth. About three hours later the platinum electrode 2 was covered so thick with a copper layer that its surface became sufficiently smooth. According to this invention, it is possible to monitor the surface condition of the copper layer as well as the plating rate $V_{ELP}$.

The plating rate $V_{ELP}$ measured by this invention was analyzed to see how similar it is to the actual plating rate. First, based on the variation of $I_{ELP}$ shown in FIG. 14 and according to equation (3), there was obtained by integration the quantity of charges $Q_{ELP}$ which had been used by five hours of electroless plating. Then, according to equation (4), where M=63.5, n=2 and F=96,500 coulombs, the weight $W_{ELP}$ of copper deposited was obtained. The weight $W_{ELP}$ thus obtained turned out to be 12.7 mg. The weight of the platinum electrode 2 plated with copper by the five fours of plating was found to be 13.4 mg heavier then the weight of the platinum electrode 2 before the plating. The measured weight $W_{ELP}$ proved quite similar to the weight of copper actually deposited on the platinum electrode 2. Hence it was ascertained that the plating rate $V_{ELP}$ measured by this invention corresponded to the actual plating rate.

Figure 15:
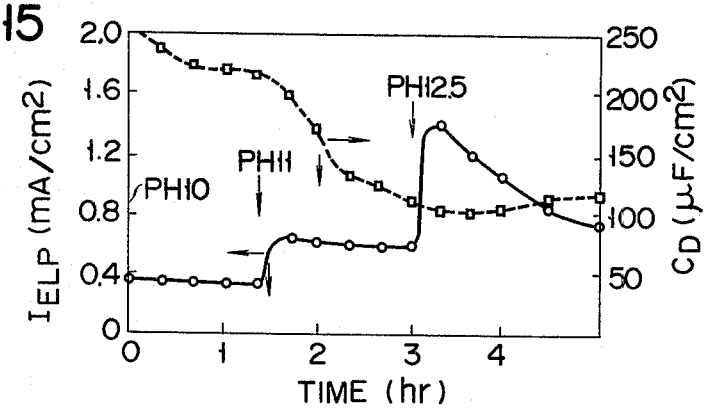

With this invention it was possible also to detect how the chemical properties of the plating bath. While changing pH of the plating bath, both the electroless deposition current density $I_{ELP}$ and the differential capacitance $C_D$ were detected and recorded. It was then observed that, as shown in FIG. 15, $I_{ELP}$, i.e. plating rate $V_{ELP}$ increased with pH value of the plating bath. On the other hand, the differential capacitance $C_D$ became smaller as pH value of the plating bath was increased, but it became a little large when pH value was 12.5. From this it is assumed that the surface of the deposited copper layer is rendered a little coarse when pH value of the plating bath was 12.5. In this way it is possible with this invention to detect precisely the plating rate $V_{ELP}$ and the surface condition of the deposited metal film in accordance with the chemical properties of the plating bath. In this experiment of analyzing the relationship between the pH value of plating bath and $I_{ELP}$ and $C_D$, it was estimated from FIG. 15 that 8.5 mg of copper was deposited on the platinum electrode 2. The weight $W_{ELP}$ measured by this invention was 8.7 mg. The electroless deposition current density $I_{ELP}$ shown in FIG. 15 was therefore proved to well correspond to the actual plating rate.

The adhesion of the copper layer to the platinum electrode 2 could be evaluated by this invention. Use was made of a plating bath which had been heated to 40° C. and whose chemical composition was as follows:

| Copper sulfate | 0.1 mol/l |
|---|---|
| EDTA | 0.175 mol/l |
| Formaldehyde | 0.05 mol/l |
| pH | 12.5 (adjusted with sodium hydroxide) |

Figure 16:
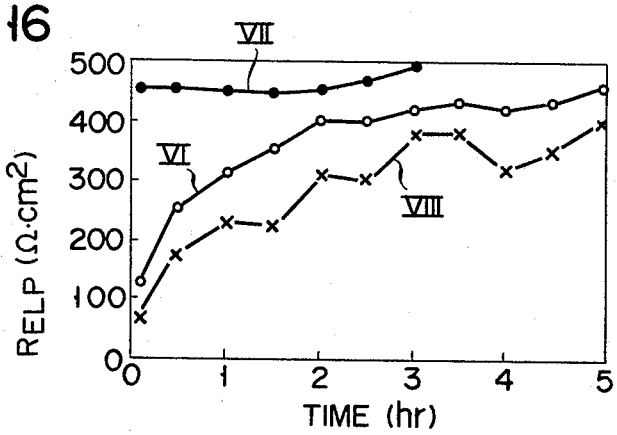

The reaction resistance $R_{ELP}$ was continuously detected to see how it would vary as time elapsed. The results were as shown in FIG. 16. Curve VI in FIG. 16 illustrates the $R_{ELP}$-time relationship when the electroless plating was carried out in normal way. Curve VII illustrates the $R_{ELP}$-time relationship when oil and fat had not been removed completely from the platinum electrode. Curve VIII shows the $R_{ELP}$-time relationship when oil and fat had not been removed and a deposited copper film peeled of the edges of the platinum electrode. By comparing curves VI, VII and VIII with curves I, II and III of FIG. 13, it could easily estimated how firmly or loosely a copper film adhered to a platinum electrode. Thus, it is possible with this invention to evaluate the adhesion of a deposited metal film to a working electrode, in a relatively short time.

Figure 17:
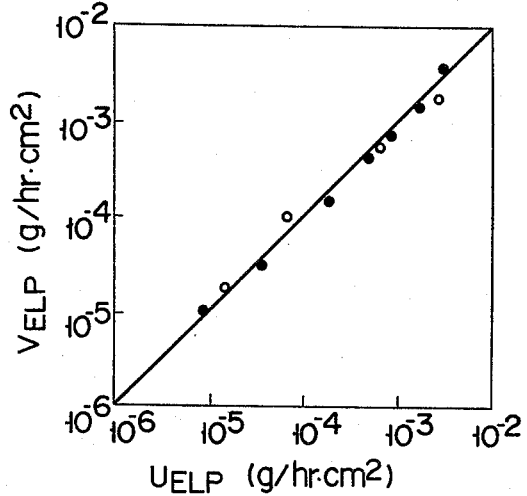

FIG. 17 shows the relationship between the rate $V_{ELP}$ at which a metal was deposited on a working electrode and which was measured by the apparatus of this invention and the rate $V_{ELP}$ at which the metal was deposited on the working electrode and which was detected by weight loss method, that is, comparing the weight of the working electrode before plating and that of the working electrode after plating. Black dots in FIG. 17 indicate the copper deposition rates obtained when use was made of plating baths of different concentration and different temperatures, each containing NaOH, copper sulfate, EDTA and Formaldehyde. White dots in FIG. 17 indicate the nickel deposition rates obtained when use was made of plating baths of different concentration and different temperatures, each containing nickel sulfate, sodium citrate, sodium acetate and ammonium chloride. As FIG. 17 shows, the metal deposition rates measured by the apparatus of this invention correspond well to the actually measured metal deposition rate. Hence, the method according to this invention is proved to measure the electroless plating rate accurately.

Figure 18:
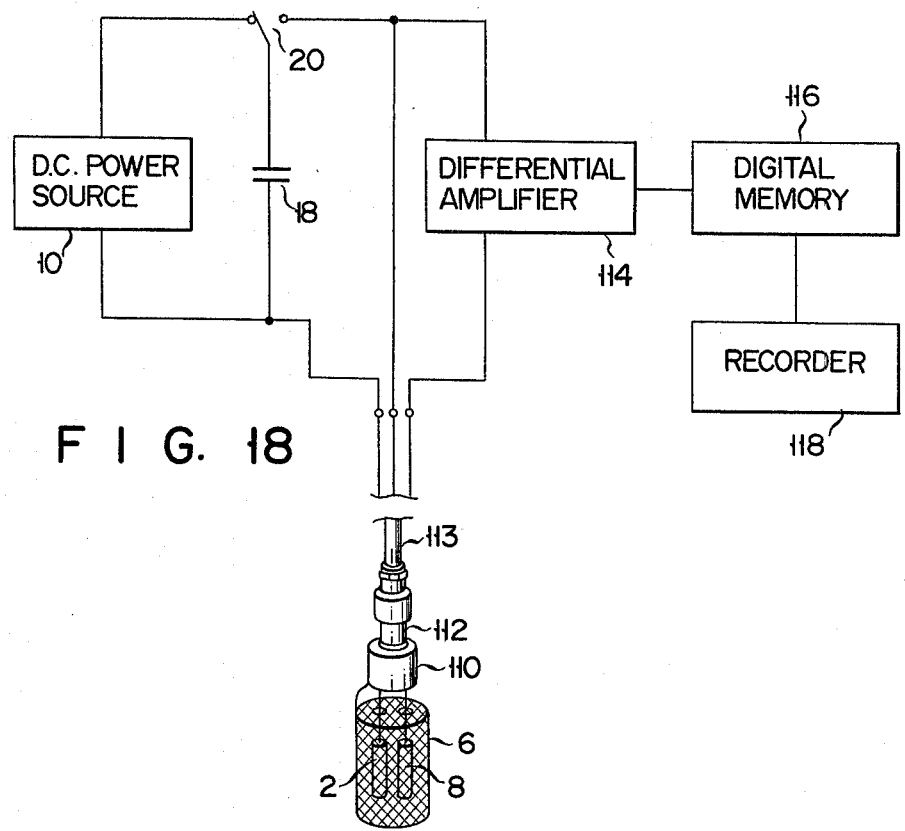
FIG. 18 is a perspective view of the arrangement of electrodes illustrated in FIG. 7 and a related circuit diagram.

Using such an apparatus as shown in FIG. 18, which is a modification of the apparatus of FIG. 7, various data were obtained. The apparatus of FIG. 18 used two oxygen free copper rods 6 mm in diameter and 30 mm long as a test piece 2 and a reference electrode 8, respectively. The test piece 2 and the reference electrode 8 were connected to a detector circuit by two lead wires sheathed with epoxy resin through a terminal 110 and a two-core shield connector 112. The apparatus used a counter electrode 6 which was a hollow cylindrical net constituted by oxygen free copper wires 0.3 mm in diameter. The hollow cylindrical net was of 80 mesh and had a diameter of 30 mm. The counter electrode 6, i.e. the hollow cylindrical net, was closed at both ends with covers. The upper cover had two holes through which the lead wires extended, and is connected to the outer core of a two-core shield cable 113 through the two-core connector 112 and thus to the detector circuit. The detector circuit is constituted by a D.C. power source 10, a relay switch 20, a differential amplifier 114, a digital memory 116 and a recorder 118.

Use was made of a plating bath which had been heated to 40° C., whose pH value was adjusted to 12 with sodium hydroxide and which contained 0.03 mol/l of copper sulfate, 0.08 mol/l of EDTA and 0.20 mol/l of formaldehyde. The plating bath was poured into a basin made of polyvinyl chloride, 40 cm long, 20 cm wide and 20 cm deep. In the basin the plating bath was stirred by an air flow blown into it. The test piece 2 and the electrodes 6 and 8 were etched for 30 seconds in a solution of ammonium persulfate, washed with water, and dried. Further they were kept immersed in a 5% sulfuric acid for 20 seconds and were then washed with water, before they were put into the plating bath.

To obtain a reaction resistance $R_{ELP}$, the D.C. power source 10 applied voltage of 11 V to a capacitor 18 having a capacitance of 0.33 $\mu$F, thus applying charge of 3.63 coulombs to the capacitor 18. The capacitor 18 was then connected to the test piece 2 and a charge was applied to the test piece 2 until its voltage was reduced to 1 V, thus applying charge of 3.3 microcoulombs to the test piece 2.

To obtain Tafel slope $\beta_a$, the D.C. power source 10 applied a voltage of 15 V to a capacitor 18 having a capacitance of 3.3 $\mu$F, thus applying a charge of 49.5 microcoulombs to this capacitor 18. This capacitor 18 was then connected to the test piece 2 and a charge was applied to the test piece 2 until its voltage was reduced to 1 V, thus applying a charge of 46.2 microcoulombs to the test piece 2.

To obtain Tafel slope $\beta_c$, the D.C. power source 10 applied a voltage of $-15$ V to a capacitor 18 having a capacitance of 3.3 to 10 $\mu$F, thus applying charge of 49.5 microcoulombs to this capacitor 18. The capacitor 18 was then connected to the test piece 2, and a charge was applied to the test piece 2 until its voltage was reduced to 1 V, thus applying charge of $-46.2$ microcoulombs to the test piece 2. These charge applications were conducted at regular intervals of about 10 minutes.

Under the above-mentioned conditions the electroless deposition current density $I_{ELP}$ was obtained in the aforementioned method. Upon lapse of an hour of electroless plating, the test piece 2 and the electrodes 6 and 8 were pulled out of the plating bath. The test piece 2, now with a copper film deposited on it, was washed with water and dried. Then its weight was measured. The current density $I_{ELP}$ was found to have varied as indicated by curve IX in FIG. 19. As curve IX shows, the electroless plating current density $I_{ELP}$ slowly decreased as time elapsed. Another curve X in FIG. 19 indicates the results obtained by an apparatus provided with a rod like counter electrode instead of the hollow cylindrical net electrode. As curve X shows, the electroless deposition current density first increases, then decreases and again increases during one hour of electroless plating. This random change in $I_{ELP}$ with time comes from uncorrect measurement of $R_{ELP}$, $\beta_a$ or $\beta_c$, which is due to induction noise or noise generated by random flow of plating bath.

Figure 19:
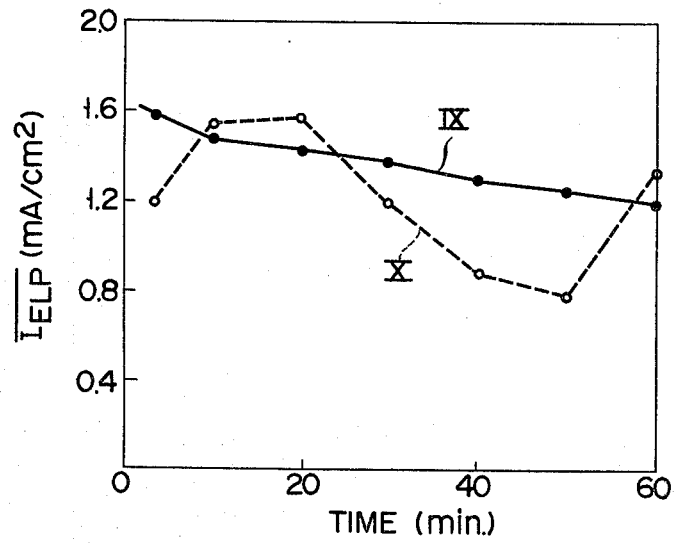
FIG. 19 is a graph showing the relationship between a lapse of time and an average $\overline{I_{ELP}}$ of an electrodes deposition current density $I_{ELP}$ obtained by the apparatus shown in FIG. 18.

Curve IX in FIG. 19 was subjected to graphical integration, thus obtaining the average $\overline{I_{ELP}}$ of the electroless deposition current density $I_{ELP}$. The average $\overline{I_{ELP}}$ turned out to be 1.32 mA/cm². Based on the atomic weight of copper, i.e. 63.5, the valence of the deposited copper ion, i.e. 2, the weight $W_{ELP}$ of the copper deposited on the test piece 2 was calculated according to equation (4). The result was 1.56 mg/cm². This means that 9.6 mg of copper had been deposited on the test piece 2. The difference between the weight of the test piece 2 before the plating and the weight of the test piece 2 after the plating was 9.4 mg. The weight $W_{ELP}$ obtained by this invention was thus proved to be nearly equal to the actual weight of the copper film deposited on the test piece 2. Hence it was ascertained that apparatus shown in FIG. 18 detected electroless deposition current density very accurately. Curve X was also subjected to graphical integration, thereby obtaining the average of electroless deposition current density and finally obtaining the weight of the copper film deposited on the test piece. The weight turned out to be 8.7 mg, whereas the actual weight of the copper film was 9.5 mg. The difference between the measured weight and the actual weight was alarmingly large.

As described above, the embodiment of this invention shown in FIG. 7 can evaluate electroless plating rate accurately and can therefore be effectively used for a large scale plating process.

As mentioned above, the method according to this invention can quickly and accurately obtain an electroless reaction resistance $R_{ELP}$, a differential capacitance $C_D$ and Tafel slopes $\beta_a$ and $\beta_c$. Based on these data it is possible to detect the plating rate, the thickness of a metal layer deposited, the surface condition of the deposited metal layer, the chemical condition of the plating bath used and the adhesion of the metal layer to the working electrode. Thus, the method of this invention can evaluate electroless plating, both quickly and accurately.

The method according to this invention is not affected by the electric resistance of the plating bath. Even if the reaction resistance is very low and the resistance of the plating bath is too high to neglect, the method can therefore evaluate electroless plating accurately. The method is also advantageous in that electrodes can be arranged in various patterns.

What we claim is:

1. A method of evaluating electroless plating, comprising the steps of:
   initiating an electroless plating reaction; and
   determining the reaction resistance $R_{ELP}$ of a test piece having a surface area S and disposed in an electroless plating bath thereby creating an electrical double layer at the interface of said test piece and said bath, said step of determining said reaction resistance comprising:
   (i) instantaneously feeding a given charge $q_R$ to the electrical double layer of the test piece, thereby changing the potential of the test piece to have a predetermined polarization potential $\eta_R$;
   (ii) measuring, as a function of time, the variation of the polarization potential $\eta_R(t)$ of the test piece due to an electroless plating reacton, using a reference electrode disposed in the plating bath;
   (iii) determining, on the basis of said polarization potential $\eta_R(t)$, an initial polarization potential $\eta_R(O)$ of the test piece upon completion of the charge supply (t=0); and
   (iv) calculating the reaction resistance $R_{ELP}$ based on the given charge $q_R$, initial polarization potential $\eta_R(0)$, surface area S and the slope of the log $\eta_R(t)-t$ relation, said reaction resistance $R_{ELP}$ being inversely proportional to the rate of electroless plating $V_{ELP}$;
   whereby electroless plating is evaluated by the reaction resistance $R_{ELP}$ thus calculated.

2. An evaluating method according to claim 1, further comprising the step of determining the Tafel slope $\beta_a$ of anodic reaction of the metal test piece, said step comprising:
   (i) instantaneously feeding the electrical double layer of the test piece with a charge $q\beta_a$ whose absolute value is larger than that of charge $q_R$, thereby changing the potential of the test piece to have a predetermined polarization potential $\eta_{\beta a}$ whose value is positive and higher than the polarization potential $\eta_R$;
   (ii) measuring, as function of time, the variation of the polarization potential $\eta_{\beta a}(t)$ of the test piece due to an electroless plating reaction, using the reference electrode; and
   (iii) calculating the Tafel slope $\beta_a$ of the test piece based on the polarization potential $\eta_{\beta a}(t)$ of the test piece measured as a function of time;
   said evaluation method also comprising the step of determining the Tafel slope $\beta_c$ of cathodic reaction of the test piece, said step comprising:
   (i) instantaneously feeding the electrical double layer of the test piece with a charge $q_{\beta c}$ whose absolute value is larger than that of the charge $q_R$ and whose polarity is opposite to that of the charge $q_{\beta a}$, thereby changing the potential of the test piece to have a predetermined polarization potential $\eta_{\beta c}$ whose value is negative;
   (ii) measuring, as a function of time, the variation of the polarization potential $\eta_{\beta c}(t)$ of the test piece due to an electroless plating reaction, using the reference electrode; and
   (iii) calculating a Tafel slope $\beta_c$ of the test piece based on the polarization potential $\eta_{\beta c}(t)$ of the test piece measured as a function of time, and said evaluation method also comprising the step of calculating the electroless plating current density $I_{ELP}$ of the test piece based on the reaction resistance $R_{ELP}$, anodic Tafel slope $\beta_a$ and cathodic Tafel slope $\beta_c$, the electroless plating current density $I_{ELP}$ being proportional to the rate of electroless plating $V_{ELP}$,
   whereby the electroless plating is evaluated by evaluating the electroless plating current density $I_{ELP}$.

3. A method according to claim 1, wherein the step of determining said initial polarization potential $\eta_R(O)$ includes the step of extrapolating the variation of the polarization potential $\eta_R(t)$ as a function of time.

4. A method according to claim 1, in which the step of calculating said reaction resistance $R_{ELP}$ includes the step of determining the differential capacitance $C_D$ of the electrical double layer of the test piece from the charge density, $\Delta q=q/S$, of the charge fed to the test piece per unit area and from the initial polarization potential $\eta_R(0)$.

5. A method according to claim 4 wherein the step of determining said differential capacitance includes the steps of dividing said charge density $\Delta q$ by said initial polarization potential $\eta_R(0)$ and wherein the step of calculating said reaction resistance $R_{ELP}$ includes the step of measuring the slope of the logarithm of $\eta_R(t)$.

6. A method according to claim 2, in which the step of determining said Tafel slope $\beta_a$ of anodic reaction includes the steps of sampling, from the polarization potential $\eta_{\beta a}(t)$, polarization potentials $\eta_{\beta a}(t_1)$, $\eta_{\beta a}(t_2)$ and $\eta_{\beta a}(t_3)$ at times $t_1$, $t_2$, and $t_3$ respectively and using the following equation:

$$\frac{\exp((-2.3/\beta_a)\eta\beta_a(t_1)) - \exp((-2.3/\beta_a)\eta\beta_a(t_2))}{\exp((-2.3/\beta_a)\eta\beta_a(t_2)) - \exp((-2.3/\beta_a)\eta\beta_a(t_3))} = \frac{t_1 - t_2}{t_2 - t_3}$$

7. A method according to claim 6, in which the step of sampling said polarization potentials includes the step of ensuring that $$\eta_{\beta a}(t_1)-\eta_{\beta a}(t_2)=\eta_{\beta a}(t_2)-\eta_{\beta a}(t_3)=\Delta\eta_{\beta a}$$

and wherein the step of obtaining Tafel slope $\beta_a$ includes the step of performing the following division:

$$a = \frac{\Delta\eta_{\beta a}}{\log\frac{t_3 - t_2}{t_1 - t_2}}$$

8. A method according to claim 2, in which the step of determining said Tafel slope $\beta_a$ of anodic reaction includes the steps of sampling the variation of the polarization potential $\eta_{\beta a}(t)$ to obtain polarization potentials $\eta_{\beta a}(t_1)$, $\eta_{\beta a}(t_2)$, $\eta_{\beta a}(t_3)$, ... $\eta_{\beta a}(t_n)$ at times $t_1$, $t_2$, $t_3$, ... $t_n$ respectively such that $$\eta_{\beta a}(t_1)-\eta_{\beta a}(t_2)=\eta_{\beta a}(t_2)-\eta_{\beta a}(t_3)= \ldots = \eta_{\beta a}(t_{n-1})-\eta_{\beta a}(t_n)=\Delta\eta_{\beta a},$$

and performing the following division:

$$\beta_a=\Delta\eta_{\beta a}/\log\delta$$

where $$\delta = \frac{1}{n-2}\left(\frac{t_3 - t_2}{t_2 - t_1} + \frac{t_4 - t_3}{t_3 - t_2} + \ldots \frac{t_n - t_{n-1}}{t_{n-1} - t_{n-2}}\right)$$

9. A method according to claim 2, in which the step of determining said Tafel slope $\beta_c$ of cathodic reaction includes the steps of sampling the variation of the polarization potential $\eta_{\beta c}(t)$ to obtain polarization potentials $\eta_{\beta c}(t_1)$, $\eta_{\beta c}(t_2)$ and $\eta_{\beta c}(t_3)$ at times $t_1$, $t_2$ and $t_3$, respectively, and performing the following division.

$$\frac{\exp((-2.3/\beta_c)\eta\beta_c(t_1)) - \exp((-2.3/\beta_c)\eta\beta_c(t_2))}{\exp((-2.3/\beta_c)\eta\beta_c(t_2)) - \exp((-2.3/\beta_c)\eta\beta_c(t_3))} = \frac{t_1 - t_2}{t_2 - t_3}$$

10. A method according to claim 9, in which the step of determining said Tafel slope $\beta_c$ includes the steps of sampling said polarization potential is carried out such that:

$$\eta_{\beta c}(t_2) - \eta_{\beta c}(t_1) = \eta_{\beta c}(t_3) - \eta_{\beta c}(t_2) = \Delta\eta_{\beta c}$$

and performing the following division:

$$c = \frac{\Delta\eta\beta_c}{\log\frac{t_3 - t_2}{t_1 - t_2}}$$

11. A method according to claim 2, in which the step of determining said Tafel slope $\beta_c$ of cathodic reaction includes the steps of sampling the variation of the polarization potentials $\eta_{\beta c}(t)$ to obtain polarization potentials $\eta_{\beta c}(t_1)$, $\eta_{\beta c}(t_2)$, $\eta_{\beta c}(t_3)$, ... $\eta_{\beta c}(t_n)$ at times $t_1$, $t_2$, $t_3$, ... $t_n$, respectively, such that $$\eta_{\beta c}(t_1) - \eta_{\beta c}(t_2) = \eta_{\beta c}(t_2) - \eta_{\beta c}(t_3) = \ldots = \eta_{\beta c}(t_{n-1}) - \eta_{\beta c}(t_n) = \Delta\eta_{\beta c}$$

and performing the following division:

$$\beta_c = \Delta\eta_{\beta c}/\log\delta$$

where $$\delta = \frac{1}{n-2}\left(\frac{t_3 - t_2}{t_2 - t_1} + \frac{t_4 - t_3}{t_3 - t_2} + \ldots \frac{t_n - t_{n-1}}{t_{n-1} - t_{n-2}}\right).$$

12. A method according to claim 1, in which said predetermined polarization potential $\eta_R$ is $-30_{mv} \leq \eta_R \leq 30_{mv}$.

13. A method according to claim 11, in which said predetermined polarization potential $\eta_R$ is $-10_{mv} \leq \eta_R \leq 10_{mv}$.

14. A method according to claim 2, in which said predetermined polarization potential $\eta_{\beta a}$ is 30 mV or more.

15. A method according to claim 13, in which the predetermined polarization potential $\eta_{\beta a}$ is +50 mV or more.

16. A method according to claim 2, in which said predetermined polarization potential $\eta_{\beta c}$ is $-30$ mV or less.

17. A method according to claim 15, in which the predetermined polarization potential $\eta_{\beta c}$ is $-50$ mV or less.

18. A method according to claim 2, including, after completion of any one of said steps, the step of applying a predetermined bias voltage to said test piece, thereby bringing the potential of the test piece back to said test piece's natural electroless deposition potential $E_{ELP}$.

19. A method according to claim 2, in which the step of calculating said electroless deposition current density $I_{ELP}$ of the test piece includes the step of performing the following multiplication:

$$I_{ELP} = (K/2.3)/R_{ELP}, \text{ where } K = \beta_a\beta_c/(\beta_a + \beta_c).$$

20. A method according to claim 19, including the step of calculating the electroless deposition rate $V_{ELP}$ of the metal test piece by performing the following multiplication:

$$V_{ELP} = (M/n \cdot F) \cdot I_{ELP},$$

where M denotes the atomic weight of the metal deposited on the test piece, n the valence of the deposited metal ion, and F the Faraday constant.

21. A method according to claim 20, including the step of calculating the weight $W_{ELP}$ of metal deposited on the test piece by performing the following multiplication:

$$W_{ELP} = (M/n \cdot F) \cdot Q_{ELP},$$

where $Q_{ELP}$ denotes the quantity of electricity consumed to deposit the metal for a period T, $Q_{ELP}$ being expressed as follows:

$$Q_{ELP} = \int_0^T I_{ELP}\,dt.$$

22. A method according to claim 3, including the step of detecting how the differential capacitance $C_D(t)$ of the electrical double layer of the test piece changes as time elapses, thus evaluating the surface condition of the metal film deposited on the test piece in accordance with the $C_D(t) - t$ relationship.

* * * * *